United States Patent
Vondruska et al.

(10) Patent No.: US 8,895,040 B2
(45) Date of Patent: Nov. 25, 2014

(54) ESTER COMPOUNDS FOR USE IN PERSONAL CARE PRODUCTS

(75) Inventors: Brian J. Vondruska, Lyndhurst, OH (US); Peter Frank, Powell, OH (US); Anchuu Wu, Broadview Heights, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 435 days.

(21) Appl. No.: 12/996,486

(22) PCT Filed: Jun. 4, 2009

(86) PCT No.: PCT/US2009/046196
§ 371 (c)(1),
(2), (4) Date: Mar. 1, 2011

(87) PCT Pub. No.: WO2009/149227
PCT Pub. Date: Dec. 10, 2009

(65) Prior Publication Data
US 2011/0195035 A1  Aug. 11, 2011

Related U.S. Application Data

(60) Provisional application No. 61/059,305, filed on Jun. 6, 2008.

(51) Int. Cl.
| | |
|---|---|
| *A61K 8/37* | (2006.01) |
| *A61Q 1/04* | (2006.01) |
| *A61Q 1/06* | (2006.01) |
| *C07C 69/604* | (2006.01) |
| *C07C 67/08* | (2006.01) |
| *C07C 69/02* | (2006.01) |
| *C07C 69/34* | (2006.01) |
| *C07C 69/76* | (2006.01) |

(52) U.S. Cl.
CPC . *A61K 8/37* (2013.01); *A61K 8/375* (2013.01); *A61Q 1/04* (2013.01); *A61Q 1/06* (2013.01)
USPC ............... 424/401; 424/405; 424/59; 424/63; 424/64; 424/65; 424/70.1; 424/70.11; 424/70.7; 554/1; 554/78; 554/85; 554/103; 554/124; 554/220; 554/223; 554/224; 554/227; 554/228; 560/1; 560/8; 560/121; 560/122; 560/125; 560/126; 560/127; 560/128; 560/129; 560/130

(58) Field of Classification Search
CPC ...... C07C 69/604; C07C 67/08; C07C 69/02; C07C 69/34; C07C 69/76; A61K 8/00; A61K 31/74; A61K 31/215; A61K 8/37; A61Q 1/06
USPC ................ 424/401, 405, 59, 63, 64, 65, 70.1, 424/70.11, 70.7; 554/1, 78, 85, 103, 124, 554/220, 223, 224, 227, 228; 560/1, 8, 121, 560/122, 125, 126, 127, 128, 129, 130; 514/506, 529, 547, 552, 553, 557, 559, 514/669, 724
See application file for complete search history.

(56) References Cited

U.S. PATENT DOCUMENTS

2004/0241198 A1  12/2004  Blin et al.

FOREIGN PATENT DOCUMENTS

| EP | 0486135 A2 | 4/1995 | |
|---|---|---|---|
| EP | 1457201 A1 | 9/2004 | |
| EP | 1491250 A1 * | 12/2004 | ............... B01F 17/34 |
| EP | 1491250 A1 * | 12/2004 | ............... B01F 17/34 |
| EP | 1857092 A1 * | 11/2007 | ............... A61K 6/00 |
| EP | 1857092 A1 * | 11/2007 | ............... A61K 6/00 |
| WO | 93/11103 A1 | 6/1993 | |
| WO | 2007/066309 A2 | 6/2007 | |

OTHER PUBLICATIONS

"Convert dalton to gram". Conversion of Measurement Units [online], [retrieved Oct. 30, 2013] Retrieved from the Internet: <URL: http//www.convertunits.com/from/dalton/to/gram.*

* cited by examiner

*Primary Examiner* — Jan C Oswecki
(74) *Attorney, Agent, or Firm* — Thoburn T. Dunlap

(57) ABSTRACT

The present invention relates to cosmetic and/or personal care formulations and/or compounds. In one embodiment, the present invention relates to ester compounds that can be used in various personal care formulations and/or compounds. In another embodiment, the present invention relates to branced ester compounds having a molecular weight of at least about 1,500 daltons that can be used in various personal care formulations and/or compounds.

12 Claims, No Drawings

ESTER COMPOUNDS FOR USE IN PERSONAL CARE PRODUCTS

CROSS REFERENCE TO RELATED APPLICATION

This application claims priority from PCT Application Serial No. PCT/US2009/046196 filed on Jun. 4, 2009, which claims the benefit of U.S. Provisional Application No. 61/059,305 filed on Jun. 6, 2008.

FIELD OF THE INVENTION

The present invention relates to personal care, home care, health care, and institutional care formulations and/or products. In one embodiment, the present invention relates to ester compounds that can be used in various personal care, home care, health care, and institutional care formulations and/or products. In another embodiment, the present invention relates to ester compounds having a molecular weight of at least about 1,500 daltons that can be used in various personal care formulations and/or products.

BACKGROUND OF THE INVENTION

Personal care product formulators are constantly trying to improve the deposition, wear, adhesion, and aesthetic properties of personal care compositions. For example, in color cosmetic compositions such as lipsticks, consumers are interested in products that wear well, feel comfortable on skin or lips, and provide nice visual aesthetics. Many consumers want a color cosmetic finish to exhibit a certain non-matte appearance because it provides lips that appear lush, dewy, and youthful. However, achieving long wearing properties often involves a trade off where comfort and shine must be sacrificed to achieve the desired long wear and transfer resistance properties. Cosmetic formulators have still not achieved the gold standard in long wearing lipsticks—a formula that provides long wear, has excellent gloss and transfer resistance, and still achieves the same comfortable feel on the lips as a lip balm.

Long wearing features are also desired in other types of color cosmetics including, but not limited to, foundation makeup, eye shadow, blush, eyeliner, lipstick, mascara, concealer, and so on. In the case of products which are not applied to the lips, the desire is to achieve long wear, while not impacting aesthetics such as finish, comfort, and removability.

Given the above, there is a need for a compound, or additive, that can impart such desirable properties to a cosmetic formulation, or compound, such as long wear and transfer resistance properties while still achieving the desired comfort level and slip when placed on an application surface.

SUMMARY OF THE INVENTION

The present invention relates to personal care, home care, health care, and institutional care formulations and/or products. In one embodiment, the present invention relates to ester compounds that can be used in various personal care home care, health care, and institutional care formulations and/or products. In another embodiment, the present invention relates to ester compounds having a molecular weight of at least about 1,500 daltons that can be used in various personal care home care, health care, and institutional care formulations and/or products. The term "personal care" as used herein includes, without limitation, cosmetics, toiletries, cosmeceuticals, beauty aids, personal hygiene and cleansing formulations and products that are applied to the skin, hair, scalp, and nails of humans and animals. The term "health care" as used herein includes, without limitation, pharmaceuticals, pharmacosmetics, oral care products (mouth, teeth), eye care products, ear care products and over-the-counter products and appliances, such as patches, plasters, dressings, and the like. The term "home care" as used herein includes, without limitation, formulations and products utilized in a household for surface protection and/or cleaning including biocidel cleaning products for maintaining sanitary conditions in the kitchen and bathroom, and laundry products for fabric cleaning and the like. The term "institutional care" as used herein includes, without limitation, formulations and products employed for protection and/or cleaning or maintaining sanitary conditions in institutional environments, including educational facilities, hospitals and health care facilities, and the like.

In one embodiment, the present invention relates to an ester composition for use in a personal care, home care, health care, and institutional care formulation comprising the reaction product of at least one poly-carboxylic acid; at least one mono-alcohol; and at least one poly-alcohol.

In another embodiment, the present invention relates to an ester composition for use in a personal care, home care, health care, and institutional care formulation comprising the stepwise reaction product of at least one poly-carboxylic acid and at least one mono-alcohol that is then reacted with at least one poly-alcohol.

In still another embodiment, the present invention relates to an ester composition for use in a personal care, home care, health care, and institutional care formulation comprising the stepwise reaction product of at least one poly-alcohol and at least one mono-carboxylic acid that is then reacted with at least one poly-carboxylic acid.

In still another embodiment, the present invention relates to an ester composition for use in a personal care, home care, health care, and institutional care formulation comprising the reaction product of at least one poly-alcohol; at least one mono-carboxylic acid; and at least one poly-carboxylic acid, wherein the resulting ester composition has a molecular weight of at least about 1,500 daltons.

In a still further embodiment, the present invention relates to an ester composition as described above for use in a cosmetic formulation or product.

DETAILED DESCRIPTION OF THE INVENTION

The present invention relates to personal care, home care, health care, and institutional care formulations and/or products. In one embodiment, the present invention relates to ester compounds that can be used in various personal care, home care, health care, and institutional care formulations and/or products. In still another embodiment, the invention relates to ester compounds that are utilized in cosmetic formulations or products. In another embodiment, the present invention relates to ester compounds having a molecular weight of at least about 1,500 daltons that can be used in various personal care (including cosmetics), home care, health care, and institutional care formulations and/or products.

In one embodiment the present invention relates to ester compositions formed from a combination of at least one poly-carboxylic acid according to the formula $R_1(C(O)OH)_n$, with about (n−1) moles of at least one mono-alcohol according to the formula $R_2OH$ and at least one crosslinking poly-alcohol according to the formula $R_3(OH)_x$, where the resulting ester composition has a molecular weight of at least about 1,500 daltons. In the at least one polycarboxylic acid, any two carboxylic acid substituents can be taken together to form an anhydride. In this embodiment, the reaction can be conducted in a batch process (i.e., where all of the reaction starting materials are combined together and then reacted). In another embodiment, the above starting materials can be reacted in a stepwise process to form the desired ester composition. In one embodiment, the —OH groups in the poly-alcohol are attached via a "$CH_2$" or "CH" moiety.

In one embodiment, $R_1$, $R_2$ and $R_3$ are independently selected from linear or branched, substituted or unsubstituted $C_1$ to $C_{60}$ hydrocarbyl groups and linear or branched, substituted or unsubstituted $C_1$ to $C_{60}$ hydrocarbondiyl groups, with the proviso that the molecular weight of the above formula must be at least about 1,500 daltons (Da) and that at least one of $R_1$, $R_2$ and $R_3$ contains one or more branched groups.

As used here and throughout the specification by "branched" or "branched group" is meant that the radical or moiety contains one or more tertiary carbon atoms (i.e., a carbon atom that is bound to at least three other carbon atoms and/or chains of carbon atoms).

As used here and throughout the specification, the term "hydrocarbyl" includes hydrocarbon as well as substantially hydrocarbon groups (e.g., ester groups or residues, etc.). Substantially hydrocarbon also includes groups which contain heteroatoms (e.g., oxygen, keto, nitrogen, phosphorus, and sulfur) which do not alter the predominantly hydrocarbon nature of the moiety. Hydrocarbyl groups are monovalent radicals having one less hydrogen atom than the parent hydrocarbon. Examples of hydrocarbyl groups include substituted and unsubstituted aliphatic (e.g., alkyl, alkenyl, alkynyl; and substituted radicals thereof); substituted and unsubstituted alicyclic (e.g., cycloalkyl, cycloalkenyl; and substituted radicals thereof); and substituted and unsubstituted $C_6$ to $C_{17}$ aromatic (e.g., phenyl, naphthyl, anthracenyl, phenanthrenyl, and substituted radicals thereof). The alicyclic and aromatic groups can be monocyclic or polycyclic. The polycyclic aromatic groups can contain non-aromatic rings fused into the ring system.

As used here and throughout the specification, the term "hydrocarbondiyl" is means a hydrocarbon group having at least two free valencies. The free valencies can be located at a terminal position(s) on the radical and/or situated on any carbon atom in the backbone of the radical. Each free valence can be covalently bonded to a functional group (e.g., a hydroxyl and/or carboxyl functional group). The hydrocarbondiyl group optionally includes ester groups or residues and/or heteroatoms (e.g., oxygen, keto, nitrogen, phosphorus, and sulfur) which do not alter the predominantly hydrocarbon nature of the moiety. Examples of hydrocarbondiyl groups include substituted and unsubstituted aliphatic (e.g., alkanediyl, alkenediyl, alkynediyl: and substituted radicals thereof); substituted and unsubstituted alicyclic (e.g., cycloalkanediyl, cycloalkenediyl; and substituted radicals thereof); and substituted and unsubstituted arenediyl (e.g., benzenediyl, naphthylenediyl, anthracenediyl, phenanthrenediyl, and substituted radicals thereof). The alicyclic and arenediyl groups can be monocyclic or polycyclic. The polycyclic arenediyl groups can contain fused non-aromatic rings in the polycyclic system. By fused is meant that a non-aromatic ring shares at least 2 common carbon atoms with an aromatic ring.

One exemplary stepwise process is illustrated in the reaction scheme below. However, the present invention is not limited to just the reaction scheme shown below. Rather, any suitable reaction scheme can be used based upon the starting materials disclosed herein.

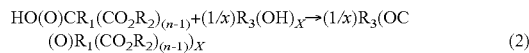

In the above embodiment, n is any integer from 2 to about 20, x is any integer from 2 to about 20, and $R_1$, $R_2$ and $R_3$ are independently selected from linear or branched, substituted or unsubstituted $C_1$ to $C_{60}$ hydrocarbyl and hydrocarbondiyl groups as previously defined. In another aspect the hydrocarbyl and hydrocarbondiyl groups defined under $R_1$, $R_2$ and $R_3$ in the embodiments above are independently selected from linear or branched, substituted or unsubstituted $C_1$ to $C_{60}$ alkyl groups in one aspect, linear or branched, substituted or unsubstituted $C_1$ to $C_{22}$ alkyl groups in another aspect, linear or branched, substituted or unsubstituted $C_1$ to $C_{12}$ alkyl groups in a further aspect, linear or branched, substituted or unsubstituted $C_1$ to $C_8$ alkyl groups in a still further aspect, and substituted or unsubstituted $C_3$ to $C_{10}$ cycloalkyl in another aspect; linear or branched, substituted or unsubstituted $C_1$ to $C_{60}$ alkanediyl groups in one aspect, linear or branched, substituted or unsubstituted $C_1$ to $C_{22}$ alkanediyl groups in another aspect, linear or branched, substituted or unsubstituted $C_1$ to $C_{12}$ alkanediyl groups in a further aspect, linear or branched, substituted or unsubstituted $C_1$ to $C_8$ alkanediyl groups in a still further aspect, and substituted or unsubstituted $C_3$ to $C_{10}$ cycloalkanediyl groups in another aspect; linear or branched, substituted or unsubstituted $C_2$ to $C_{60}$ alkenyl groups in one aspect, linear or branched, substituted or unsubstituted $C_2$ to $C_{22}$ alkenyl groups in another aspect, linear or branched, substituted or unsubstituted $C_2$ to $C_{12}$ alkenyl groups in a further aspect, linear or branched, substituted or unsubstituted $C_2$ to $C_8$ alkenyl groups in a still further aspect, and substituted or unsubstituted $C_3$ to $C_{10}$ cycloalkenyl in another aspect; linear or branched, substituted or unsubstituted $C_2$ to $C_{60}$ alkenediyl groups in one aspect, linear or branched, substituted or unsubstituted $C_2$ to $C_{22}$ alkenediyl groups in another aspect, linear or branched, substituted or unsubstituted $C_2$ to $C_{12}$ alkenediyl groups in a further aspect, linear or branched, substituted or unsubstituted $C_2$ to $C_8$ alkenediyl groups in a still further aspect, and substituted or unsubstituted $C_3$ to $C_{10}$ cycloalkenediyl in another aspect; linear or branched, substituted or unsubstituted $C_2$ to $C_{60}$ alkynyl groups in one aspect, linear or branched, substituted or unsubstituted $C_2$ to $C_{22}$ alkynyl groups in another aspect, linear or branched, substituted or unsubstituted $C_2$ to $C_{12}$ alkynyl groups in a further aspect, and linear or branched, substituted or unsubstituted $C_2$ to $C_8$ alkynyl groups in a still further aspect; linear or branched, substituted or unsubstituted $C_2$ to $C_{60}$ alkynediyl groups in one aspect, linear or branched, linear or branched, substituted or unsubstituted $C_2$ to $C_{22}$ alkynediyl groups in another aspect, linear or branched, substituted or unsubstituted $C_2$ to $C_{12}$ alkynediyl groups in a further aspect, and linear or branched, substituted or unsubstituted $C_2$ to $C_8$ alkynediyl groups in a still further aspect; substituted or unsubstituted $C_6$ to $C_{17}$ aryl groups in one aspect, substituted or unsubstituted $C_6$ to $C_{10}$ aryl groups in another aspect, and substituted or unsubstituted $C_6$ aryl groups in a further aspect; substituted or unsubstituted $C_6$ to $C_{17}$ arenediyl groups in one aspect, substituted or unsubstituted $C_6$ to $C_{10}$ arenediyl groups in another aspect, and substituted or unsubstituted $C_6$ arenediyl groups in a further aspect; or linear or branched $C_2$ to $C_{60}$ ester groups, with the proviso that the molecular weight of the compounds represented by the above formula must be at least about 1,500 daltons (Da) and that at least one of $R_1$, $R_2$ and $R_3$ contains one or more branched groups.

In another embodiment, the ester compounds according to the above reaction schemes have a viscosity of less than about 1000 mPa·s (milliPascals·sec).

As used here and throughout the specification, the term "alkanediyl" is defined to mean an alkane group having at least two free valencies. The free valencies can be located at a terminal position(s) on the radical and/or situated on any carbon atom in the backbone of the radical. The carbon atom in which a free valence is situated is available for covalently bonding a functional group (e.g., a hydroxyl and/or carboxyl functional group). For illustrative purposes non-limiting examples of linear and branched alkanediyl moieties are (the lines attached to only a single carbon atom represent a free valence):

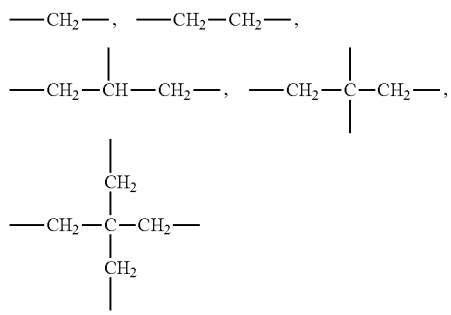

As used here and throughout the specification, the term "cycloalkanediyl" refers to cyclic or polycyclic alkane moieties having at least two free valencies. The free valencies can be located on any carbon atom in the ring. The carbon atom in which a free valence is situated is available for covalently bonding a functional group (e.g., a hydroxyl and/or carboxyl functional group).

As used here and throughout the specification, the term "alkenediyl" means an alkene group having one or more carbon-carbon double bonds and at least two free valencies. The free valencies can be located at a terminal position(s) on the radical and/or situated on any carbon atom in the backbone of the radical. The carbon atom in which a free valence is situated is available for covalently bonding a functional group (e.g., a hydroxyl and/or carboxyl functional group). For illustrative purposes non-limiting examples of linear and branched alkenediyl moieties are (the lines attached to only a single carbon atom represent a free valence):

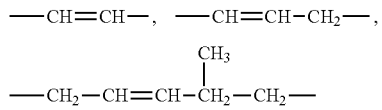

As used here and throughout the specification, the term "cycloalkenediyl" refers to cyclic or polycyclic alkene moieties having one or more carbon-carbon double bonds and at least two free valencies. The free valencies can be located on any carbon atom in the ring. The carbon atom in which a free valence is situated is available for covalently bonding a functional group (e.g., a hydroxyl and/or carboxyl functional group).

As used here and throughout the specification, the term "alkyndiyl" means an alkene group having one or more carbon-carbon triple bonds and at least two free valencies. The free valencies can be located at a terminal position(s) on the radical and/or situated on any carbon atom in the backbone of the radical. The carbon atom in which a free valence is situated is available for covalently bonding a functional group (e.g., a hydroxyl and/or carboxyl functional group). For illustrative purposes non-limiting examples of linear and branched alkynediyl moieties are (the lines attached to only a single carbon atom represent a free valence):

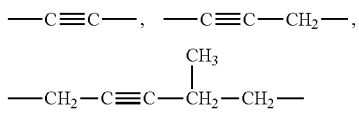

As used here and throughout the specification, the term "arenediyl" means an arene group (monocyclic or polycyclic) having at least two free valencies that are not part of a double bond. The free valencies can be located on any carbon atom in the ring or ring system. The carbon atom in which a free valence is situated is available for covalently bonding a functional group (e.g., a hydroxyl and/or carboxyl functional group). The polycyclic arenediyl groups may contain fused non-aromatic rings in the polycyclic system. By fused is meant that a non-aromatic ring shares at least 2 common carbon atoms with an aromatic ring. For illustrative purposes non-limiting examples of arenediyl moieties are (the line projecting from a ring represents a free valence):

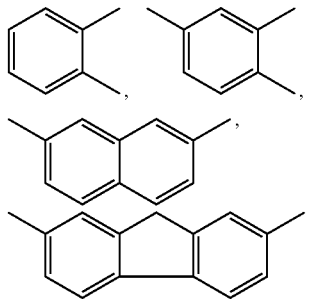

While the free valencies depicted in the exemplary arenediyl moieties set forth above are situated on specific carbon atoms in a ring, it is recognized that a free valence can be positioned at any carbon atom in the ring system.

As used above and throughout the specification a "substituted" radical means that the radical is substituted by at least one substituent. In one embodiment the at least one substituent is selected from $C_1$ to $C_{10}$ alkyl, $C_3$ to $C_{10}$ cycloalkyl, $C_3$ to $C_{10}$ cycloalkenyl, $C_6$ to $C_{14}$ aryl, $C_7$ to $C_{18}$ arylalkyl, $C_1$ to $C_{10}$ alkoxy, carboxyl, carboxy($C_1$ to $C_{10}$)alkyl, hydroxyl, hydroxy($C_1$ to $C_{10}$)alkyl, amino, mono-($C_1$ to $C_{10}$)alkylamino, di-($C_1$ to $C_5$)alkylamino, mono-($C_1$ to $C_5$)alkylamino ($C_1$ to $C_{10}$)alkyl, di-($C_1$ to $C_5$)alkylamino($C_1$ to $C_{10}$)alkyl, halo (bromo, chloro, fluoro, iodo), mercapto, mercapto($C_1$ to $C_{10}$)alkyl, sulfo, ($C_1$ to $C_5$) alkylthio, ($C_1$ to $C_5$) alkylsulfinyl, ($C_1$ to $C_5$) alkylsulfonyl, nitro, and combinations thereof.

In still another embodiment, the molecular weight of the ester compounds of the present invention are at least about 2,000 daltons, at least about 2,500 daltons, at least about 5,000 daltons, or even at least about 7,500 daltons. In still another embodiment, the esters of the present invention have a viscosity of less than about 750 mPa·s, less than about 500 mPa·s, less than about 400 mPa·s, less than about 300 mPa·s, less than about 200 mPa·s, or even less than about 100 mPa·s.

Here, as well as elsewhere in the specification and claims, individual numerical values, or limits, can be combined to form non-disclosed and/or non-stated ranges.

Regarding the molecular weights stated herein, such molecular weights are determined by gel permeation chromatography (GPC) using a Bishoff-2250 Pump instrument, with the following parameters: Mobile Phase: tetrahydrofuran, 250 ppm butylated hydroxytoluene, 1.0 mL/min; Injector: Waters 717 Plus Autosampler; Sample Size: 50 μL. Filtered at room temperature with a 0.45μ PTFE filter; Column Set: PL Gel Mixed-E+100 A, both 7.5×300 mm, 3μ, 40° C.; Detector: Waters 2414 DRI Detector; Computer: Dell OptiPlex 270 with Waters Empower Pro LC/GPC Software, Version 6.00. The molecular weight calibration is established using EasiCal polystyrene standards from Polymer Laboratories having a molecular weight range from $7.5 \times 10^6$ to 162. Unless specifically noted, molecular weight ranges and values disclosed and reported in the specification and claims herein are number average molecular weight ($M_w$) values.

Regarding the viscosity values stated herein, such viscosity values are determined by the Brookfield rotating spindle method: The viscosity of each composition is reported as mPa·s and is measured with a Brookfield rotating spindle viscometer, Model RVT (Brookfield Engineering Laboratories, Inc.), at about 20 revolutions per minute (rpm), at ambient room temperature of about 20° C. to 25° C. (herein referred to as simply viscosity), and with a spindle size of 62.

In another embodiment, the ester compositions of the present invention contain at least 2 ester groups per molecule, at least 3 ester groups per molecule, at least 4 ester groups per molecule, or at least 5 or more ester groups per molecule. In another embodiment, the ester compositions of the present invention contain at least about 7 ester groups per molecule, at least about 10 ester groups per molecule, at least about 12 ester groups per molecule, or at least about 15 ester groups per molecule, or even at least about 20 or more ester groups per molecule. Again in this embodiment, such compounds should possess a molecular weight of at least about 1,500 daltons, at least about 2,000 daltons, at least about 2,500 daltons, at least about 5,000 daltons, or even at least about 7,500 daltons.

In another embodiment, the esters of the present invention exhibit a high contact angle as measured, for example, by placing a drop of the ester on a Vitro-skin® substrate (IMS, Milford, Conn.) and measuring the contact angle using a DataPhysics OCA20 contact angle measuring instrument. By high contact angle it is meant that the contact angle measurement described above is in the range of about 20° to about 120°, or in the range from about 30° to about 90°, or even in the range of about 40° to about 80°.

In still another embodiment the present invention relates to ester compositions formed from a combination of at least one poly-alcohol according to the formula $R_4(OH)_m$, with about (m−1) moles of at least one mono-carboxylic acid according to the formula $R_5C(O)OH$ and at least one crosslinking polycarboxylic acid according to the formula $R_6(C(O)OH)_y$, where the resulting ester composition has a molecular weight of at least about 1,500 daltons. In the at least one crosslinking polycarboxylic acid, any two carboxylic acid substituents can be taken together to form an anhydride. In this embodiment, the reaction can be conducted in a batch process (i.e., where all of the reaction starting materials are combined together and then reacted). In another embodiment, the above starting materials can be reacted in a stepwise process to form the desired ester composition. In another embodiment, the above starting materials can be reacted in a stepwise process to form the desired ester composition. In one embodiment, the —OH groups in the poly-alcohol are attached via a "$CH_2$" or "CH" moiety. One exemplary stepwise process is illustrated in the reaction scheme below. However, the present invention is not limited to just the reaction scheme shown below. Rather, any suitable reaction scheme can be used based upon the starting materials disclosed herein.

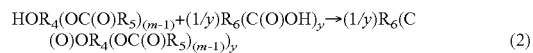

In one embodiment, $R_4$, $R_5$ and $R_6$ are independently selected from linear or branched, substituted or unsubstituted $C_1$ to $C_{60}$ hydrocarbyl groups and linear or branched, substituted or unsubstituted $C_1$ to $C_{60}$ hydrocarbondiyl groups, with the proviso that the molecular weight of the above formula must be at least about 1,500 daltons (Da) and that at least one of $R_4$, $R_5$ and $R_6$ contains one or more branched groups. The terms hydrocarbyl and hydrocarbondiyl are as previously defined. In another embodiment, the ester compounds produced according to the above reaction schemes have a viscosity of less than about 1000 mPa·s (milliPascals·sec).

In the above embodiments, m is any integer from 2 to about 20, y is any integer from 2 to about 20. In another aspect, the hydrocarbyl and hydrocarbondiyl groups set forth under $R_4$, $R_5$ and $R_6$ above are independently selected from linear or branched, substituted or unsubstituted $C_1$ to $C_{60}$ alkyl groups in one aspect, linear or branched, substituted or unsubstituted $C_1$ to $C_{22}$ alkyl groups in another aspect, linear or branched, substituted or unsubstituted $C_1$ to $C_{12}$ alkyl groups in a further aspect, linear or branched, substituted or unsubstituted $C_1$ to $C_8$ alkyl groups in a still further aspect, and substituted or unsubstituted $C_3$ to $C_{10}$ cycloalkyl groups in another aspect; linear or branched, substituted or unsubstituted $C_1$ to $C_{60}$ alkanediyl groups in one aspect, linear or branched, substituted or unsubstituted $C_1$ to $C_{22}$ alkanediyl groups in another aspect, linear or branched, substituted or unsubstituted $C_1$ to $C_{12}$ alkanediyl groups in a further aspect, linear or branched, substituted or unsubstituted $C_1$ to $C_8$ alkanediyl groups in a still further aspect, and substituted or unsubstituted $C_3$ to $C_{10}$ cycloalkanediyl groups in another aspect; linear or branched, substituted or unsubstituted $C_2$ to $C_{60}$ alkenyl groups in one aspect, linear or branched, substituted or unsubstituted $C_2$ to $C_{22}$ alkenyl groups in another aspect, linear or branched, substituted or unsubstituted $C_2$ to $C_{12}$ alkenyl groups in a further aspect, linear or branched, substituted or unsubstituted $C_2$ to $C_8$ alkenyl groups in a still further aspect, and substituted or unsubstituted $C_3$ to $C_{10}$ cycloalkenyl groups in another aspect; linear or branched, substituted or unsubstituted $C_2$ to $C_{60}$ alkenediyl groups in one aspect, linear or branched, substituted or unsubstituted $C_2$ to $C_{22}$ alkenediyl groups in another aspect, linear or branched, substituted or unsubstituted $C_2$ to $C_{12}$ alkenediyl groups in a further aspect, linear or branched, substituted or unsubstituted $C_2$ to $C_8$ alkenediyl groups in a still further aspect, and substituted or unsubstituted $C_3$ to $C_{10}$ cycloalkenediyl groups in another aspect; linear or branched, substituted or unsubstituted $C_2$ to $C_{60}$ alkynyl groups in one aspect, linear or branched, substituted or unsubstituted $C_2$ to $C_{22}$ alkynyl groups in another aspect, linear or branched, substituted or unsubstituted $C_2$ to $C_{12}$ alkynyl groups in a further aspect, and linear or branched, substituted or unsubstituted $C_2$ to $C_8$ alkynyl groups in a still further aspect; linear or branched, substituted or unsubstituted $C_2$ to $C_{60}$ alkynediyl groups in one aspect, linear or branched, substituted or unsubstituted $C_2$ to $C_{22}$ alkynediyl groups in another aspect, linear or branched, substituted or unsubstituted $C_2$ to $C_{12}$ alkynediyl groups in a further aspect, and linear or branched, substituted or unsubstituted $C_2$ to $C_8$ alkynediyl groups in a still further aspect; substituted or unsubstituted $C_6$ to $C_{17}$ aryl groups in one aspect, substituted or unsubstituted $C_6$ to $C_{10}$ aryl groups in another aspect, and substituted or unsubstituted $C_6$ aryl groups in a further aspect; substituted or unsubstituted $C_6$ to $C_{17}$ arenediyl groups in one aspect, substituted or unsubstituted $C_6$ to $C_{10}$ arenediyl groups in another aspect, and substituted or unsubstituted $C_6$ arenediyl groups in a further aspect; or linear or branched $C_2$ to $C_{60}$ ester groups, with the proviso that the molecular weight of the compounds represented by the above formula must be at least about 1,500 daltons (Da) and that at least one of $R_4$, $R_5$ and $R_6$ contain one or more branched groups. In another embodiment, the ester compounds produced according to the above reaction schemes have a viscosity of less than about 1000 mPa·s (milliPascals·sec).

In still another embodiment, the molecular weight of the ester compounds of the present invention are at least about 2,000 daltons, at least about 2,500 daltons, at least about 5,000 daltons, or even at least about 7,500 daltons. In still another embodiment, the esters of the present invention have a viscosity of less than about 750 mPa·s, less than about 500 mPa·s, less than about 400 mPa·s, less than about 300 mPa·s, less than about 200 mPa·s, or even less than about 100 mPa·s. Here, as well as elsewhere in the specification and claims, individual numerical values, or limits, can be combined to form non disclosed and/or non-stated ranges.

In another embodiment, the ester compositions of the present invention contain at least 2 ester groups per molecule, at least 3 ester groups per molecule, at least 4 ester groups per molecule, or at least 5 or more ester groups per molecule. In another embodiment, the ester compositions of the present invention contain at least about 7 ester groups per molecule, at least about 10 ester groups per molecule, at least about 12 ester groups per molecule, or at least about 15 ester groups per molecule, or even at least about 20 or more ester groups per molecule. Again in this embodiment, such compounds should possess a molecular weight of at least about 1,500 daltons, at least about 2,000 daltons, at least about 2,500 daltons, at least about 5,000 daltons, or even at least about 7,500 daltons.

In one embodiment the ester compositions of the present invention can be used for, among other things, an additive in any suitable personal care formulation, including cosmetics, where long wear and transfer resistance properties are desired without sacrificing comfort and slip. Such personal care formulations in which the esters of the present invention can be used include, but are not limited to, lipstick, foundation makeup, eye shadow, blush, eyeliner, lipstick, mascara, concealer, and so on. In another embodiment, the esters of the present invention are present in an amount in the range of about 0.1 weight percent to about 75 weight percent of the total weight of the personal care, home care, health care, and institutional care formulation. In another embodiment, the esters of the present invention are present in an amount in the range of about 1 weight percent to about 70 weight percent, of from about 2.5 weight percent to about 65 weight percent, or from about 5 weight percent to about 60 weight percent, or from about 7.5 weight percent to about 55 weight percent, or from about 10 weight percent to about 50 weight percent, or from about 12.5 weight percent to about 45 weight percent, or from about 15 weight percent to about 40 weight percent, or from about 20 weight percent to about 35 weight percent, or even from about 25 weight percent to about 30 weight percent of the total weight of the personal care, home care, health care, and institutional care formulation. In still another embodiment, the esters of the present invention are present in for example, a lipstick formulation in an amount in the range of about 35 weight percent to about 55 weight percent. In still another embodiment, the esters of the present invention are present in, for example, a personal care emulsion in an amount in the range of about 2.5 weight percent to about 7.5 weight percent.

The molecular weight of the esters of the present invention can be adjusted to achieve optimal long wear and transfer resistance properties in combination with the desired comfort and slip properties. The molecular weight can vary from about 1,500 daltons to about 100,000 daltons, or from about 2,000 daltons to about 75,000 daltons, or even from about 2,500 daltons to about 50,000 daltons. In one embodiment, the stoichiometry of the acid groups and hydroxyl groups is near equivalent and might be expected to vary by about 1, about 2, or about 3 mole percent up to about 10 mole percent. Hydroxyl numbers of less than about 40, less than about 35, less than about 30, less than about 25, less than about 20, less than about 15, less than about 10, less than about 8, less than about 5, or even less than about 3 mg KOH/g polymer are desirable. Acid numbers of less than about 40, less than about 35, less than about 30, less than about 25, less than about 20 less than about 15, less than about 10, less than about 8, less than about 5, or even less than about 3 mg KOH/g polymer are desirable. Here, as well as elsewhere in the specification and claims, individual numerical values, or limits, can be combined to form non-disclosed and/or non-stated ranges.

In one embodiment, the ester compositions of the present invention help to impart long wear properties to a personal care product. In one instance long wear is determined by transfer resistance over time. In another embodiment, the esters of the present invention possess less tack than other personal care esters of similar molecular weight. By similar molecular weight, it is meant that the two esters being compared for tack have molecular weights within about plus or minus 20 percent, or even about plus or minus 10 percent.

The esters of the present invention can be produced via a variety of processes known in the art. For example, the esters of the present invention can be produced via a condensation reaction. In this case, it is desirable to purge water out of the reactants to push the condensation reaction towards completion. A suggested procedure used to make the esters of the present invention includes, but is not limited to, mixing the reactants in a stirred reactor under an inert gas such as nitrogen and at a temperature of about 130° C. to about 255° C. until both the acid and hydroxyl values are acceptable (e.g., normally the reaction is stopped at an acid or hydroxyl number between about 3 to about 40 mg KOH/g of product in one aspect, between about 3 to about 35 mg KOH/g of product in another aspect, between about 3 to about 25 mg KOH/g of product in still another aspect, and 3 to about 20 mg KOH/g of product in a further aspect). In another embodiment, the process to produce the esters of the present invention utilizes a suitable catalyst. Such catalysts are known to those of skill in the art and include, but are not limited to, suitable homogenous or heterogeneous tin, palladium and/or platinum catalysts.

Exemplary Poly-Carboxylic Acids:

As used herein a poly-carboxylic acid (i.e., a polyfunctional carboxylic acid) is any composition that contains two or more carboxylic acid groups, and optionally one or more additional functional groups and/or substituents, including functionalized and non-functionalized dicarboxylic acids. The poly-carboxylic acids of the present invention can be aliphatic, cycloaliphatic, aromatic, saturated, linear and/or branched. In one embodiment, the poly-carboxylic acids used herein have 2 to about 60 carbon atoms, or from 2 to about 45 carbon atoms, or even from 2 to about 30. Such compounds include, but are not limited to, oxalic acid, malonic acid, succinic acid, glutaric acid, adipic acid, azelaic acid, sebacic acid, dimer dilinoleic acid, trilinoleic acid, dodecanedioic acid, maleic acid, fumaric acid, phthalic acid, isophthalic acid, terephthalic acid, 2,6-naphthalene dicarboxylic acid, citric acid, malic acid, tartaric, butane tertracarboxylic acid, derivatives thereof or anhydrides thereof (e.g., phthalic anhydride, trimellitic anhydride, succinic anhydride, maleic anhydride) or any suitable combination of two or more thereof.

In another embodiment, the poly-carboxylic acid, or acids, of the present invention is/are selected from one or more compounds according to the formula $R_1(C(O)OH)_n$ or $R_6(C(O)OH)_y$ where n and y are independently selected from any integer from 2 to about 20, and $R_1$ and $R_6$ are as previously defined.

Exemplary Mono-Alcohols:

As used herein a mono-alcohol is any compound that contains one hydroxyl (—OH) group, and optionally one or more additional functional groups, including functionalized (substituted) and non-functionalized (non-substituted) alcohols. The mono-alcohols of the present invention can be aliphatic, cycloaliphatic, aromatic, saturated, linear and/or branched. Additionally, the hydroxyl group of the mono-alcohols of the present invention can be a primary, secondary, or tertiary hydroxyl group. In one embodiment, the mono-alcohols used herein have 1 to about 60 carbon atoms, or from 1 to about 45 carbon atoms, or even from 1 to about 30. Such compounds include, but are not limited to, behenyl alcohol, phenol, benzyl alcohol, naphthol, butanol, butyldecanol, butyloctanol, cetyl alcohol, decyl alcohol, decyltetraedecanol, dodecylhexadecanol, ethanol, ethylhexanol, heptanol, hexadecyloctadecanol, hexanol, cyclohexanol, hexyldecanol, hexyloctanol, isobutanol, isocetyl alcohol, isodecyl alcohol, isohexyl alcohol, isononyl alcohol, isopropanol, isostearyl alcohol, lauryl alcohol, methanol, myristyl alcohol, octadodecyl alcohol, octanol, octyldecanol, oleyl alcohol, pentanol, propanol, stearyl alcohol, tetradecyloctadecanol, derivatives thereof, or any suitable combination of two or more thereof.

In another embodiment, the mono-alcohol, or mono-alcohols, of the present invention is/are selected from one or more compounds according to the formula $R_2OH$ where $R_2$ is as previously defined. It should be noted that in this embodiment, depending upon the nature of $R_2$, the mono-alcohols could again be primary, secondary, or tertiary alcohols.

In still another embodiment, the mono-alcohol of the present invention is a mixture of two or more mono-alcohols where each alcohol making up such a mixture can be chosen from a primary, secondary or tertiary alcohol. Accordingly, in this instance, the mono-alcohol portion of the present invention can be a mixture of any combination of primary, secondary or tertiary alcohols. Thus, it is possible to have all one type of mono-alcohol (e.g., all primary mono-alcohols) or to have a mixture of different types of alcohols (e.g., a combination of one or more primary mono-alcohols with one or more secondary alcohols).

Exemplary Poly-Alcohols:

As used herein a poly-alcohol is any composition that contains two or more hydroxyl groups, and optionally one or more additional functional groups, including functionalized and non-functionalized alcohols. The poly-alcohols of the present invention can be aliphatic, aromatic, saturated, linear and/or branched. Additionally, the two or more hydroxyl groups of the poly-alcohols of the present invention can include any combination of primary, secondary, or tertiary hydroxyl groups. In one embodiment, the poly-alcohols used herein have 1 to about 60 carbon atoms, or from 1 to about 45 carbon atoms, or even from 1 to about 30. Such compounds include, but are not limited to, diols, triols, tetraois, pentaols, hexaols that may be linear and/or branched, aliphatic and/or aromatic. In one embodiment, suitable poly-alcohols include, but are not limited to, glycerol, polyglycerol-X (where X is an integer from 2 to about 20, or even from 2 to about 10), pentaerythritol, dipentaerythrityl, tripentaerythritol, trimethylolpropane, neopentyl glycol, propylene glycol, 1,3-butylene glycol, 2-methyl-1,3-propanediol, dipropylene glycol, ethylene glycol, cyclohexane-dimethanol, butyl ethyl propanediol, resorcinol, hydroquinone, and derivatives thereof, dimethyloipropanoic acid, dimethylol butanoic acid, or any suitable combination of two or more thereof.

In another embodiment, the poly-alcohol, or poly-alcohols, of the present invention is/are selected from one or more compounds according to the formula $R_3(OH)_x$, $R_3(CH_2OH)$, $R_4(OH)_m$, or $R_4(CH_2OH)_m$ where x and m and $R_3$ and $R_4$ are as previously defined.

Exemplary Mono-Carboxylic Acids:

As used herein a mono-carboxylic acid (i.e., a monofunctional carboxylic acid) is any composition that contains one carboxylic acid group, and optionally one or more additional functional groups or substituents, including functionalized and non-functionalized carboxylic acids. The mono-carboxylic acids of the present invention can be aliphatic, aromatic, saturated, linear and/or branched. In one embodiment, the mono-carboxylic acids used herein have 1 to about 60 carbon atoms, or from 1 to about 45 carbon atoms, or even from 1 to about 30. Such compounds include, but are not limited to, isobutyric acid, benzoic acid, 2-ethyl butyric acid, hexanoic acid, heptanoic acid, 2-ethylhexanoic acid, octanoic acid, nonanoic acid, 3,5,5-trimethylhexanoic acid, isononanoic acid, decanoic acid, isooctadecanoic acid, dodecanoic acid, 2-methyl butyric acid, isopentanoic acid, pentanoic acid, 2-methyl pentanoic acid, 2-methyl hexanoic acid, isooctanoic acid, undecylinic acid, isolauric acid, isopalmitic acid, isostearic acid, behenic acid, glycolic acid, propiolic acid, lactic acid, pyruvic acid, acetoacetic acid, cinnamic acid, and derivatives thereof, or any suitable combination of two or more thereof.

In another embodiment, the mono-carboxylic acid, or acids, of the present invention is/are selected from one or more compounds according to the formula $R_5C(O)OH$ where $R_5$ is as previously defined.

Examples of Polymeric Polyol Esters:

The following are exemplary ester compositions in accordance with various embodiments of the present invention. It is noted however that the present invention is not limited to just the following embodiments but rather the present invention should be broadly construed.

Experimental Ester 1 (Tris(Glyceryl Diisostearate) Trimellitate):

A glass reactor equipped with a stirrer, thermometer, nitrogen inlet and water trap connected to a condenser is charged with 803.20 grams of isostearic acid, 12520 grams of glycerin, 1.90 grams of methanesulfonic acid (70%), and 0.90 grams of hypophosphorous acid (50%). The reaction mixture is heated to about 170° C. or about 1 hour while removing water from the reaction. After holding the reaction at the aforementioned temperature for about 2 hours 68.80 grams of trimellitic anhydride is added and the reaction temperature is increased to about 210° C. and maintained at this temperature while removing water from the reaction until the total acid or hydroxyl number is less than about 5 mg KOH/g. The total reaction time is typically 16 to 24 hours.

Experimental Ester 2 (Tris(Glyceryl Diisostearate) Citrate):

A glass reactor equipped with a stirrer, thermometer, nitrogen inlet and water trap connected to a condenser is charged with 800.70 grams of isostearic acid, 125.80 grams of glycerin, 1.90 grams of methanesulfonic acid (70%), and 0.90 grams of hypophosphorous acid (50%). The reaction mixture is heated to about 170° C. for about 1 hour while removing water from the reaction. After holding the reaction at the aforementioned temperature for about 2 hours 70.70 grams of citric acid is added and the reaction temperature is increased to about 220° C. and maintained at this temperature while removing water from the reaction until the total acid or hydroxyl number is less than about 5 mg KOH/g. The total reaction time is typically 16 to 24 hours.

Experimental Ester 3 (Tris(TMP Diisostearate) Trimellitate):

A glass reactor equipped with a stirrer, thermometer, nitrogen inlet and water trap connected to a condenser is charged with 780.30 grams of isostearic acid, 162.60 grams of trimethylolpropane, 1.90 grams of methanesulfonic acid (70%), and 0.90 grams of hypophosphorous acid (50%). The reaction mixture is heated to about 180° C. for about 1 hour while removing water from the reaction. After holding the reaction at the aforementioned temperature for about 2 hours 54.30 grams of trimellitic anhydride is added and the reaction temperature is increased to about 210° C. and maintained at this temperature while removing water from the reaction until the total acid or hydroxyl number is less than about 5 mg KOH/g. The total reaction time is typically 16 to 24 hours.

Experimental Ester 4 (Tris(Polyglyceryl-3-Tetraisostearate) Citrate):

A glass reactor equipped with a stirrer, thermometer, nitrogen inlet and water trap connected to a condenser is charged with 812.70 grams of isostearic acid, 160.50 grams of polyglyceryl-3, 2.00 grams of methanesulfonic acid (70%), and 1.00 gram of hypophosphorous acid (50%). The reaction mixture is heated to about 145° C. for about 1 hour while removing water from the reaction. After holding the reaction at the aforementioned temperature for about 4 hours 23.80 grams of citric acid is added and the reaction is maintained at 145° C. while removing water from the reaction until the total acid or hydroxyl number is less than about 5 mg KOH/g. The total reaction time is typically 16 to 24 hours.

Experimental Ester 5: (Bis(Trimethylolpropyl Dicocoate) Adipate)

A glass reactor equipped with a stirrer, thermometer, nitrogen inlet and water trap connected to a condenser is charged with 678.20 grams of coconut fatty acid, 100.20 grams of adipic acid, 220.60 grams of trimethylolpropane, and 1.00 gram of hypophosphorous acid (50%). The reaction mixture is heated to about 180° C. for about 2 hours while removing water from the reaction. After holding the reaction at the aforementioned temperature for about 2 hours, the reaction temperature is increased to about 240° C. to 245° C. and maintained at this temperature while removing water from the reaction until the total acid or hydroxyl number is less than about 5 mg KOH/g and the kinematic viscosity at 100° C. is between about 200 mPa·s to about 320 mPa·s. The total reaction time is typically 16 to 24 hours.

Viscosity and Molecular Weight Data for Examples 1 Through 5:

Table 1 below details the viscosity data and molecular weight data determined using the methods discussed above for Examples 1 through 5. It should be noted that unless otherwise specified the viscosity of the samples are determined at 22° C.

TABLE 1

|  | Viscosity (mPa · s) | Molecular Weight (Da) |
| --- | --- | --- |
| Experimental Ester 1 | 835 | 3455 |
| Experimental Ester 2 | 352 | 1877 |
| Experimental Ester 3 | 812 | 2822 |
| Experimental Ester 4 | 910 | 3278 |
| Experimental Ester 5 | 302 (at 25° C.) | 3402 |

In one embodiment of the invention, the ester compounds of the present invention permit, facilitate and/or enhance the delivery, deposition and/or activity of one or more active ingredients utilized in a personal care, home care, health care, and institutional care formulations, and for improving the psychosensory and aesthetic properties of a topical formulation in which they are included. Examples of such active ingredients include, but are not limited to, caffeine, vitamin C, vitamin D, vitamin E, anti-stretch mark compounds, astringents (e.g., alum, oatmeal, yarrow, witch hazel, bayberry, and isopropyl alcohol), draining compounds, hair growth compounds (e.g., monoxidil), skin and hair nourishing compounds, skin and hair protecting compounds, self-tanning compounds (e.g., mono- or polycarbonyl compounds such as, for example, isatin, alloxan, ninhydrin, glyceraldehyde, mesotartaric aldehyde, glutaraldehyde, erythrulose, tyrosine, tyrosine esters, and dihydroxyacetone), sunscreens (e.g., ethylhexyl methoxy cinnamate, octinoxate, octisalate, oxybenzone), skin lighteners (e.g., kojic acid, hydroquinone, arbutin, fruital, vegetal or plant extracts, such as lemon peel extract, chamomile, green tea, paper mulberry extract, and the like, ascorbyl acid derivatives, such as ascorbyl palmitate, ascorbyl stearate, magnesium ascorbyl phosphate, and the like), lip plumping compounds, anti-aging, anti-cellulite, and anti-acne compounds (e.g., acidic agents such as alpha-hydroxy acids (AHAs), beta-hydroxy acids (BHAs), alpha amino-acids, alpha-keto acids (AKAs), acetic acid, azelaic acid, and mixtures thereof), anti-dandruff compounds (e.g., zinc pyrithione, zinc omadine, miconazole nitrate, selenium sulfide, piroctone olamine) anti-inflammatory compounds (e.g., aspirin, ibuprofen, and naproxen), analgesics (e.g., acetaminophen), antioxidant compounds, antiperspirant compounds (e.g., aluminum halides, aluminum hydroxyhalides, aluminum sulfate, zirconium (zirconyl) oxyhalides, zirconium (zirconyl)hydroxyhalides, and mixtures or complexes thereof), deodorant compounds (e.g., 2-amino-2-methyl-1-propanol (AMP), ammonium phenolsulfonate; benzalkonium chloride; benzethonium chloride, bromochlorophene, cetyltrimethylammonium bromide, cetyl pyridinium chloride, chlorophyllin-copper complex, chlorothymol, chloroxylenol, cloflucarban, dequalinium chloride, dichlorophene, dichloro-m-xylenol, disodium dihydroxyethyl sulfosuccinylundecylenate, domiphen bromide, hexachlorophene, lauryl pyridinium chloride, methylbenzethonium chloride, phenol, sodium bicarbonate, sodium phenolsulfonate, triclocarban, triclosan, zinc phenolsulfonate, zinc ricinoleate, and mixtures thereof), hair fixative polymers (e.g., natural and synthetic polymers such as, for example, polyacrylates, polyvinyls, polyesters, polyurethanes, polyamides, modified cellulose, starches, and mixtures thereof), hair and skin conditioners (e.g., synthetic oils, natural oils, such as vegetable, plant and animal oils, mineral oils, natural and synthetic waxes, cationic polymers, monomeric and polymeric quaternized ammonium salt compounds, silicones such as silicone oils, resins and gums, proteins, hydrolyzed proteins, fatty acids, fatty amines; and mixtures thereof); and suitable mixtures of two or more of the above.

Unless otherwise stated herein, the active ingredients are present in effective amounts to accomplish their function, and are generally included individually at a level of from 0 wt. % to 30 wt %, based on the weight of the total composition in which they are employed.

Suitable AHAs include, but are not limited to, lactic acid, glycolic acid, fruit acids, such as malic acid, citric acid, tartaric acid, extracts of natural compounds containing AHA, such as apple extract, apricot extract, and the like, honey extract, 2-hydroxyoctanoic acid, glyceric acid (dihydroxypropionic acid), tartronic acid (hydroxypropanedioic acid), gluconic acid, mandelic acid, benzilic acid, alpha-lopioc acid, AHA salts and derivatives, such as arginine glycolate, ammonium lactate, sodium lactate, alpha-hydroxybutyric acid, alpha-hydroxyisobutyric acid, alpha-hydroxyisocaproic acid, alpha-hydroxyisovaleric acid, atrolactic acid, and the like. Suitable BHAs include, but are not limited to, 3-hydroxy propanoic acid, beta-hydroxybutyric acid, beta-phenyl lactic acid, beta-phenylpyruvic acid, salicylic acid, and the like. Suitable alpha-amino acids include, without being limited to, alpha-amino dicarboxylic acids, such as aspartic acid, glutamic acid, and the like. Representative alpha-keto acids are pyruvic acid, acetopyruvic acid, and the like. Other active acidic agents include retinoic acid and its derivatives, halocarboxylic acids (e.g., trichloroacetic acid), acidic antioxidants (e.g., vitamin C), mineral acids, phytic acid, lysophosphatidic acid, salicylic acid, derivatives of salicylic acid (e.g., 5-octanoylsalicylic acid), and the like.

The fixative polymers can be nonionic, anionic, cationic and amphoteric in nature and include without limitation one or more of polyoxythylenated vinyl acetate/crotonic acid copolymers, vinyl acetate crotonic acid copolymers, vinyl methacrylate copolymers, monoalkyl esters of poly(methyl vinyl ether (PVM)/maleic acid (MA)), such as, for example, ethyl, butyl and isopropyl esters of PVM/MA copolymer acrylic acid/ethyl acrylate/N-tert-butyl-acrylamide terpolymers, and poly(methacrylic acid/acrylamidomethyl propane sulfonic acid), acrylates copolymer, octylacrylamide/acrylates/butylaminoethyl methacrylate copolymer, acrylates/octylacrylamide copolymer, vinyl acetate (VA)/crotonates/vinyl neodeanoate copolymer, poly(N-vinyl acetamide), poly (N-vinyl formamide), corn starch modified, sodium polystyrene sulfonate, polyquaterniums such as, for example, Polyquaternium-4, Polyquaternium-11, Polyquaternium-24, Polyquaternium-28, Polyquaternium-29, Polyquaternium-32, Polyquaternium-34, Polyquaternium-37, Polyquaternium-39, Polyquaternium-44, Polyquaternium-46, Polyquaternium-47, Polyquarternium-55, Polyquaternium-69, Polyquaternium-87, polyether-1, polyurethanes, VA/acrylates/lauryl methacrylate copolymer, adipic acid/dimethylaminohydroxypropyl diethylene AMP/acrylates copolymer, methacrylol ethyl betaine/acrylates copolymer, polyvinylpyrrolidone (PVP), vinyl pyrrolidone (VP)/dimethylaminoethylmethacrylate copolymer, VP/methacrylamide/vinyl imidazole copolymer, VP/dimethylaminopropylamine (DMAPA) acrylates copolymer, VP/vinylcaprolactam/DMAPA acrylates copolymer, VP/dimethylaminoethylmethacrylate copolymer, VP/DMAPA acrylates copolymer, vinyl caprolactam/VP/dimethylaminoethyl methacrylate copolymer, VA/butyl maleate/isobornyl acrylate copolymer, VA/crotonates copolymer, acrylate/acrylamide copolymer. VA/crotonates/vinyl propionate copolymer, VP/vinyl acetate/vinyl propionate terpolymers, VA/crotonates, VP/vinyl acetate copolymer, VP/acrylates copolymer, VA/crotonic acid/vinyl proprionate, acrylates/acrylamide, acrylates/octylacrylamide, acrylates/hydroxyacrylates copolymer, acrylates/hydroxyesteracrylates copolymer, acrylates/stereth-20 methacrylate copolymer, tert-butyl acrylate/acrylic acid copolymer, diglycol/cyclohexanedimethanol/isophthalates/sulfoisophthalates copolymer, VA/butyl maleate and isobornyl acrylate copolymer, vinylcaprolactam/VP/dimethylaminoethyl methacrylate, VA/alkylmaleate half ester/N-substituted acrylamide terpolymers, vinyl caprolactam/VP/methacryloamidopropyl trimethylammonium chloride terpolymer, methacrylates/acrylates copolymer/amine salt, polyvinylcaprolactam, polyurethanes, hydroxypropyl guar, poly(methacrylic acid/acrylamidomethyl propane sulfonic acid (AMPSA), ethylenecarboxamide (EC)/AMPSA/methacrylic acid (MAA), poylurethane/acrylate copolymers and hydroxypropyl trimmonium chloride guar, acrylates copolymer, acrylates crosspolymer, AMP-acrylates/allyl methacrylate copolymer, polyacrylate-14, polyacrylate-2 crosspolymer, octylacrylamide/acrylates/butylaminoethyl methacrylate copolymer, acrylates/octylacrylamide copolymer, VA/crotonates/vinyl neodeanoate copolymer, poly(N-vinyl acetamide), poly(N-vinyl formamide), polyurethane, acrylates/lauryl acrylate/stearyl acrylate/ethylamine oxide methacrylate copolymer, methacryloyl ethyl betaines/methacrylates copolymer, corn starch modified, sodium polystyrene sulfonate, polyurethane/acrylates copolymer, pyrrolidone carboxylic acid salt of chitosan, chitosan glycolate, cationic polygalactomannans, such as, for example, quaternized derivatives of guar, such as, for example, guar hydroxypropyl trimmonium chloride and hydroxypropyl guar hydroxypropyl trimmonium chloride. Many of the foregoing polymers are referred to by their INCI nomenclature set forth in the International Cosmetic Ingredient Dictionary published by the Cosmetic, Toiletry, and Fragrance Association, Washington D.C. Other suitable auxiliary fixative polymers are disclosed in U.S. Pat. No. 7,205,271, the disclosure of which is herein incorporated by reference.

The fixative polymer(s), alone or in combination with the optional auxiliary fixative(s), typically comprises about 0.01 wt. % to about 25 wt. % in one aspect, from about 0.1 wt. % to about 10 wt. % in another aspect, and about 0.2 wt. % to about 5 wt. % in a further aspect of the total weight of the composition.

Referring to exemplary conditioners, the synthetic oil conditioners include polyolefins, e.g., poly-α-olefins such as polybutenes, polyisobutenes and polydecenes. The polyolefins can be hydrogenated. Fluorinated or perfluorinated oils are also contemplated within the scope of the present invention. Fluorinated oils include perfluoropolyethers described in European Patent 0 486 135 and the fluorohydrocarbon compounds described in WO 93/11103. The fluoridated oils may also be fluorocarbons such as fluoramines, e.g., perfluorotributylamine, fluoridated hydrocarbons, such as perfluorodecahydronaphthalene, fluoroesters, and fluoroethers.

Suitable natural oil conditioners include but are not limited to peanut, sesame, avocado, coconut, cocoa butter, almond, safflower, corn, cotton seed, sesame seed, walnut oil, castor, olive, jojoba, palm, palm kernel, soybean, wheat germ, linseed, sunflower seed; eucalyptus, lavender, vetiver, litsea, cubeba, lemon, sandalwood, rosemary, chamomile, savory, nutmeg, cinnamon, hyssop, caraway, orange, geranium, cade, and bergamot oils, fish oils, glycerol tricaprocaprylate; and mixtures thereof.

Suitable natural and synthetic wax conditioning agents include but are not limited to carnauba wax, candelila wax, alfa wax, paraffin wax, ozokerite wax, olive wax, rice wax, hydrogenated jojoba wax, bees wax, modified bees wax, e.g., cerabellina wax, marine waxes, polyolefin waxes, e.g., polyethylene wax; and mixtures thereof.

Representative cationic polymer conditioners include but are not limited to homopolymers and copolymers derived from free radically polymerizable acrylic or methacrylic ester or amide monomers. The copolymers can contain one or more units derived from acrylamides, methacrylamides, diacetone acrylamides, acrylic or methacrylic acids or their esters, vinyllactams such as vinyl pyrrolidone or vinyl caprolactam, and vinyl esters. Exemplary polymers include copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone/dialkylaminoalkyl acrylate or methacrylate, optionally quaternized, such as the products sold under the name GAFQUAT™ by International Specialty Products; the dimethyl amino ethyl methacrylate/vinyl caprolactam/vinyl pyrrolidone terpolymers, such as the product sold under the name GAFFIX™ VC 713 by International Specialty Products; the vinyl pyrrolidone/methacrylamidopropyl dimethylamine copolymer, marketed under the name STYLEZE™ CC 10 by International Specialty Products; and the vinyl pyrrolidone/quaternized dimethyl amino propyl methacrylamide copolymers such as the product sold under the name GAFQUAT™ HS 100 by International Specialty Products.

Cationic polymer conditioners can also be selected from the quaternary polymers of vinyl pyrrolidone and vinyl imidazole such as the products sold under the trade name Luviquat® (product designation FC 905, FC 550, and FC 370) by BASF. Other cationic polymer conditioners that can be used in the compositions of the invention include polyalkyleneimines such as polyethyleneimines, polymers containing vinyl pyridine or vinyl pyridinium units, condensates of polyamines and epichlorhydrins, quaternary polyurethanes, and quaternary derivatives of chitin.

Other non-limiting examples of quaternary ammonium compounds useful as cationic conditioners in the present invention include acetamidopropyl trimonium chloride, behenamidopropyl dimethylamine, behenamidopropyl ethyldimonium ethosulfate, behentrimonium chloride, cetethyl morpholinium ethosulfate, cetrimonium chloride, cocoamidopropyl ethyldimonium ethosulfate, dicetyldimonium chloride, dimethicone hydroxypropyl trimonium chloride, hydroxyethyl behenamidopropyl dimonium chloride, quaternium-26, quaternium-27, quaternium-53, quaternium-63, quaternium-70, quaternium-72, quaternium-76 hydrolyzed collagen, PPG-9 diethylmonium chloride, PPG-25 diethylmonium chloride, PPG-40 diethylmonium chloride, stearalkonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, polymers and copolymers of dimethyl diallyl ammonium chloride, such as Polyquaternium-4, Polyquaternium-6, Polyquaternium-7, Polyquaternium-10, Polyquaternium-11, Polyquarternium-16, Polyquaternium-22, Polyquaternium-24, Polyquaternium-28, Polyquaternium-29, Polyquaternium-32, Polyquaternium-33, Polyquaternium-35, Polyquaternium-37, Polyquaternium 39, Polyquaternium-44, Polyquaternium-46, Polyquaternium-47, Polyquaternium-52, Polyquaternium-53, Polyquarternium-55, Polyquaternium-59, Polyquaternium-61, Polyquaternium-64, Polyquaternium-65, Polyquaternium-67, Polyquaternium-69, Polyquaternium-70, Polyquaternium-71, Polyquaternium-72, Polyquaternium-73, Polyquaternium-74, Polyquaternium-76, Polyquaternium-77, Polyquaternium-78, Polyquaternium-79, Polyquaternium-80, Polyquaternium-81, Polyquaternium-82, Polyquaternium-84, Polyquaternium-85, Polyquaternium-87, PEG-2-cocomonium chloride.

Silicones useful as conditioning agents can be present in the form of fluids, oils, waxes, resins, gums, and mixtures thereof. They can be volatile or non-volatile and soluble or insoluble in the composition. The silicones can be selected from polyalkyl siloxanes, polyaryl siloxanes, polyalkyl aryl siloxanes, polyorgano siloxanes modified by organofunctional groups, and mixtures thereof. The silicones suitable for use according to the invention include the silicone containing polymers and copolymers described in the emulsifier and emollient disclosure below.

Suitable polyalkyl siloxanes include polydimethyl siloxanes with terminal trimethyl silyl groups or terminal dimethyl silanol groups (dimethiconol) and polyalkyl ($C_1$-$C_{20}$) siloxanes.

Suitable polyalkyl aryl siloxanes include polydimethyl methyl phenyl siloxanes and polydimethyl diphenyl siloxanes, linear or branched.

The silicone gums suitable for use herein include polydiorganosiloxanes. In one aspect the silicone gums have a number-average molecular weight between 200,000 and 1,000,000 daltons. Examples include polymethyl siloxane, polydimethyl siloxane/methyl vinyl siloxane gums, polydimethyl siloxane/diphenyl siloxane, polydimethyl siloxane/phenyl methyl siloxane and polydimethyl siloxane/diphenyl siloxane/methyl vinyl siloxane.

Suitable silicone resins include silicones with a dimethyl/trimethyl siloxane structure and resins of the trimethyl siloxysilicate type.

The organo-modified silicones suitable for use in the invention include silicones containing one or more organo-functional groups attached by means of a hydrocarbon radical and grafted siliconated polymers. Exemplary organo-modified silicones are amino functional silicones.

The conditioning agent can be a protein or hydrolyzed cationic or non-cationic protein. Examples of these compounds include hydrolyzed collagens having triethyl ammonium groups, hydrolyzed collagens having trimethyl ammonium and trimethyl stearyl ammonium chloride groups, hydrolyzed animal proteins having trimethyl benzyl ammonium groups (benzyltrimonium hydrolyzed animal protein), hydrolyzed proteins having quaternary ammonium moieties on the polypeptide chain, including at least one $C_1$-$C_{18}$ alkyl moiety. Hydrolyzed proteins include Croquat™ L, in which the quaternary ammonium groups include a $C_{12}$ alkyl group, Croquat™ M, in which the quaternary ammonium groups include $C_{10}$-$C_{18}$ alkyl groups, Croquat™ S in which the quaternary ammonium groups include a $C_{16}$ alkyl group and Crotein™ Q in which the quaternary ammonium groups include at least one $C_1$-$C_{18}$ alkyl group. These products are sold by Croda International, Quaternized vegetable proteins such as wheat, corn, or soy proteins such as cocodimonium, hydrolyzed wheat protein, laurdimonium hydrolyzed wheat protein and steardimonium hydrolyzed wheat protein are also useful as conditioning agents.

Suitable fatty acids that can be used as conditioning agents are those previously described as emulsifiers, including $C_{12}$-$C_{22}$ fatty acids. Exemplary fatty acid conditioners include but are not limited to myristic acid, palmitic acid, stearic acid, oleic acid, linoleic acid, isostearic acid, and behenic acid.

Suitable fatty amines known to be useful as a conditioning agent: e.g., dodecyl, cetyl or stearyl amines, such as stearamidopropyl dimethylamine are also useful in the compositions of the invention.

The conditioning agent(s) can be present in an amount of 0.001 wt. % to 20 wt. % in one aspect, from 0.01 wt. % to 10 wt. % in another aspect, and from 0.1 wt. % to 3 wt. % based on the total weight of the personal care composition.

The ester compounds of the present invention are suitable additives for a wide variety of personal care, health care, home care, and institutional care formulations or products some of which include one or more of the active ingredients enumerated above. Non-limiting examples of such personal care, home care, health care, and institutional care formulations or products are set forth below.

The ester compounds of the present invention are suitable additives for the formulation of hair setting and style maintenance compositions which contain hair conditioners, hair fixatives, or hair relaxing agents. Such compositions can be in the form of aerosol and non-aerosol hair sprays, spritzes, gels, spray gels, pomades, mousses, styling creams, and the like. The ester compounds of the present invention are compatible with dyes and pigments suitable to prepare colored hair setting and style maintenance products.

The ester compositions of the present invention are also suitable additives for the preparation of shampoos, two-in-one conditioning shampoos, conditioners, rinses, bath and shower gels, liquid soap, soap bars, conditioning liquid bath oil, bubble bath, bath powders, and the like.

The ester compositions of the present invention are suitable for the preparation of personal care (cosmetics, toiletries, cosmeceuticals) and topical health care products, including without limitation, skin care products (facial, body, hands, scalp, and feet), such as creams, lotions, conditioners, and cleansing products; anti-acne products; anti-aging products (exfoliant, keratolytic, anti-cellulite, anti-wrinkle, and the like); skin protectants such as sunscreens, sun blocks, barrier creams, antiseptics, disinfectants, insect repellents, itch relief compositions, oils, silicones, and the like; skin color products (whiteners, lighteners, sunless tanning accelerators, and the like); hair colorants (hair dyes, hair color rinses, highlighters, bleaches and the like); pigmented skin colorants (face and body makeups, foundation creams, mascara, rouge, eye shadow, lip products, such as lip sticks, lip balms, lip glosses, lip creams, and the like); nail care products (water-based polishes, polish removers, strengtheners, lengtheners, hardeners, cuticle removers, softeners, and the like; hair-removal products (shaving creams and lotions, depilatories, aftershave skin conditioners, and the like); deodorants and antiperspirants; oral care products (mouth, teeth, and gums), such as mouthwash, dentifrice, such as toothpaste, tooth powder, tooth polishes, tooth whiteners, breath fresheners, denture adhesives, and the like; facial and body hair bleach, and the like. Other health and beauty aids that can contain the esters of the invention without limitation, include sunless tanning compositions, face care products (e.g., anti-wrinkle, anti-acne, and anti-aging compositions), skin depigmenting, whitening, and lightening formulations; foot care products, such as keratolytic corn and callous removers, foot soaks, foot powders (medicated, such as antifungal athlete's foot powder, ointments, sprays, and the like, and antiperspirant powders, or non-medicated moisture absorbent powder), liquid foot sprays (non-medicated, such as cooling, and deodorant sprays, and medicated antifungal sprays, antiperspirant sprays, and the like), and foot and toenail conditioners (lotions and creams, nail softeners, and the like).

In the formulation of health care products the ester compounds of the invention can be incorporated as an additive in topically applied pharmaceuticals in the form of creams, pomades, gels, pastes, ointments, gels, or in medical applications as an additive in disinfectant hand creams, antiviral and antibiotic ointments, sprays, and creams. The esters can be utilized as an additive in purgative fluids (enemas, emetics, colonics, and the like), anti-fungal foams, eye products (ophthalmic products, such as eye drops, artificial tears, active drug delivery fluids, contact lens cleaner, and the like), ear products (wax softeners, wax removers, otitis drug delivery drops, and the like), nasal products (drops, ointments, sprays, and the like), and wound care (liquid bandages, wound dressings, antibiotic creams, ointments, and the like), drug delivery compositions to deliver transdermally active ingredients to or through the skin (topical analgesics, anti-inflammatory, motion sickness, and the like).

In home care and institutional, for example, the esters of the invention can be incorporated to improve formulation efficiency through "cling-on-surface" to improve the efficacy of fabric conditioning agents, antistatic agents, and disinfectants. Typical household and institutional care products that can contain the esters of the invention, include, without limitation, laundry and fabric care products, such as detergents, fabric softeners (liquids or sheets), ironing sprays, dry cleaning aids, anti-wrinkle sprays, laundry pre-spot removers, spot removers, and the like; hard surface cleansers for the kitchen and bathroom and utilities and appliances employed or located therein, such as toilet bowl gels, tub and shower cleaners, hard water deposit removers, floor and tile cleansers, wall cleansers, floor and chrome fixture polishes, alkali-strippable vinyl floor cleaners, natural polished stone, synthetic stone, and ceramic cleaners, air freshener gels, liquid cleansers for dishes, and the like; disinfectant cleaners, such as toilet bowl and bidet cleaners, disinfectant hand soaps, room deodorizers, and the like.

The ester compositions of the invention function to promote or enhance the deposition and/or transdermal delivery of active ingredients in topical medical compositions to or through the skin. The esters promote the surface deposition of active ingredients (e.g., dandruff control agents, conditioners, antistatic agents, disinfectants) from shampoos, conditioners, detergents, disinfectants, cleaners, salves, and the like, and enhance the deposition of colorants on skin from pigmented cosmetics (makeups, lipsticks, rouges, and the like) and on hair from hair dyes; and the like.

In one embodiment the ester compounds in accordance with the present invention can be used in a host of cosmetic applications where various properties such as long wear and transfer resistance are desired without potentially sacrificing comfort level and slip. Given this, the ester compounds of the present invention can be used as additives in cosmetic formulations, antiperspirant and deodorant formulations, removable protective coatings, wound dressings, etc.

In another embodiment the esters of the invention can be used with the one or more of the personal care, health care, home care, and institutional care active ingredients, discussed above in combination with one or more additives and/or adjuvants, conventionally or popularly included in personal care, health care, home care, and institutional care products. Such additives and/or adjuvants include, but are not limited to the following: solvents, acidifying pH adjusting agents, alkalizing pH adjusting agents and buffering agents, film formers, fillers, rheology modifiers (e.g., Carbopol® or Pemulen® polymers from Lubrizol Advanced Materials, Inc.), emulsifiers, emulsion stabilizers, waxes, dispersants, viscosity control agents, solvents, electrolytes, auxiliary conditioning agents, non-surfactant suspending aids, glossifiers, penetrants, antistatic agents, synthetic oils, vegetable or animal oils, silicone oils, monomeric or polymeric quaternized ammonium compounds and derivatives thereof, sheen enhancers, moisturizers, emollients, humectants, lubricants, oxidizing agents; reducing agents; surfactants, such as anionic, cationic, nonionic, amphoteric, zwitterionic surfactants, polymer film modifying agents (e.g., plasticizers, tackifiers, detackifiers, wetting agents, and the like) chelating agents, opacifiers, pearlescing agents, proteinaceous materials and derivatives thereof, vitamins and derivatives thereof, preservatives, fragrances, solubilizers, colorants, dyes, pigments (temporary or permanent), UV absorbers, propellants (water-miscible or water-immiscible), such as fluorinated hydrocarbons, liquid volatile hydrocarbons, compressed gases, and the like, natural and derivatized hydrocolloids, such as guar and cassia gums and the quaternized derivatives thereof (e.g., hydroxypropyl trimmonium chloride guar and 2-hydroxy-3-(trimethylammonium)propyl Cassia galactomannan chloride; and mixtures thereof.

In one embodiment of the invention, one or more of the ester compositions disclosed herein can be used in combination with one or more of the disclosed personal care, health care, home care, and institutional care active ingredients. In another embodiment, one or more of the ester compositions of the invention can be used in combination with one or more of the disclosed additives and/or adjuvants. In a further embodiment, one or more of the ester compositions can be utilized in combination with one or more of the disclosed additives and/or adjuvants and one or more of the personal care, health care, home care, and institutional care active ingredients disclosed herein.

Non-limiting examples of acidifying or acidic pH adjusting agents include organic acids, such as citric acid, acetic acid, alpha-hydroxy acid, beta-hydroxy acid, salicylic acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized. Non-limiting examples of alkalizing or alkaline pH adjusting agents include ammonia, alkali metal hydroxides, such as sodium hydroxide, and potassium hydroxide; ammonium hydroxide, alkanolamines such as mono-, di- and triethanolamine; diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis (hydroxypropyl)ethylenediamine; and alkali metal salts of inorganic acids, such as sodium borate (borax), sodium phosphate, sodium pyrophosphate, and the like, and mixtures thereof.

Suitable buffering agents include but are not limited to alkali or alkali earth carbonates, phosphates, bicarbonates, citrates, borates, acetates, acid anhydrides, succinates and the like, such as sodium phosphate, citrate, borate, acetate, bicarbonate, and carbonate.

The pH adjusting agent is utilized in any amount necessary to obtain a desired pH value in the personal composition. In one aspect, the fixative composition of the invention can contain at least one alkalizing (alkaline pH adjusting agent) or acidifying agent (acidic pH adjusting agent) in amounts from 0.01 to 30 wt. % of the total weight of the composition.

Fillers include but are not limited to silicas, silicates, nylon powder, poly(methyl methacrylate) (PMMA), Teflon® powder, boron nitride, starches and flours (rice, corn, wheat, potato), talc, mica, sericite, kaolin, carbonates, polyethylene, polypropylene, polyethylene copolymers, polytetrafluoroethylene, bismuth oxychloride, lauroyl lysine, powdered acrylates copolymers, and maltodextrin.

Rheology modifiers can be included in the compositions of the invention not only for their ability to thicken compositions in which they are employed but also as formulation stabilizers and/or suspending aids. Suitable rheology modifiers include synthetic and semi-synthetic rheology modifiers. Exemplary synthetic rheology modifiers include acrylic based polymers and copolymers. One class of acrylic based rheology modifiers are the carboxyl functional alkali-swellable and alkali-soluble thickeners (ASTs) produced by the free-radical polymerization of acrylic acid alone or in combination with other ethylenically unsaturated monomers. The polymers can be synthesized by solvent/precipitation as well as emulsion polymerization techniques. Exemplary synthetic rheology modifiers of this class include homopolymers of acrylic acid or methacrylic acid and copolymers polymerized from one or more monomers of acrylic acid, substituted acrylic acid, and salts and $C_1$-$C_{30}$ alkyl esters of acrylic acid and substituted acrylic acid. As defined herein, the substituted acrylic acid contains a substituent positioned on the alpha and/or beta carbon atom of the molecule wherein the substituent is preferably and independently selected from $C_{1-4}$ alkyl, —CN, and —COOH. Optionally, other ethylenically unsaturated monomers such as, for example, styrene, vinyl acetate, ethylene, butadiene, acrylonitrile, as well as mixtures thereof can be copolymerized into the backbone. The foregoing polymers are optionally crosslinked by a monomer that contains two or more moieties that contain ethylenic unsaturation. In one aspect, the crosslinker is selected from a polyalkenyl polyether of a polyhydric alcohol containing at least two alkenyl ether groups per molecule. Other Exemplary crosslinkers are selected from allyl ethers of sucrose and allyl ethers of pentaerythritol, and mixtures thereof. These polymers are more fully described in U.S. Pat. No. 5,087,445; U.S. Pat. No. 4,509,949; and U.S. Pat. No. 2,798,053 herein incorporated by reference.

In one embodiment the AST rheology modifier is a crosslinked homopolymer polymerized from acrylic acid or methacrylic acid and is generally referred to under the INCI name of Carbomer. Commercially available Carbomers include Carbopol® polymers 934, 940, 941, 956, 980 and 996 available from Lubrizol Advanced Materials, Inc. In another embodiment the AST rheology modifier is selected from a crosslinked copolymer polymerized from a first monomer selected from one or more monomers of (meth)acrylic acid, substituted acrylic acid, and salts of (meth)acrylic acid and substituted acrylic acid and a second monomer selected from one or more $C_1$-$C_5$ alkyl acrylate esters of (meth)acrylic acid. These polymers are designated under the INCI name of Acrylates Copolymer. Acrylates Copolymers are commercially available under the trade names Aculyn® 33 from Rohm and Haas and Carbopol® Aqua SF-1 from Lubrizol Advanced Materials, Inc. In a further aspect the rheology modifier is selected from a crosslinked copolymer polymerized from a first monomer selected from one or more monomers of acrylic acid, substituted acrylic acid, salts of acrylic acid and salts of substituted acrylic acid and a second monomer selected from one or more $C_{10}$-$C_{30}$ alkyl acrylate esters of acrylic acid or methacrylic acid. In one aspect the monomers can be polymerized in the presence of a steric stabilizer such as disclosed in U.S. Pat. No. 5,288,814 which is herein incorporated by reference. Some of the forgoing polymers are designated under INCI nomenclature as Acrylates/C10-30 Alkyl Acrylate Crosspolymer and are commercially available under the trade names Carbopol® 1342 and 1382, Carbopol® Ultrez 20 and 21, Carbopol® ETD 2020 and Pemulen® TR-1 and TR-2 from Lubrizol Advanced Materials, Inc. Any vinyl or acrylic based rheology modifiers are suitable.

Another class of synthetic rheology modifiers suitable for use in the present invention includes hydrophobically modified ASTs commonly referred to as hydrophobically modified alkali-swellable and alkali-soluble emulsion (HASE) polymers. Typical HASE polymers are free radical addition polymers polymerized from pH sensitive or hydrophilic monomers (e.g., acrylic acid and/or methacrylic acid), hydrophobic monomers (e.g., $C_1$-$C_{30}$ alkyl esters of acrylic acid and/or methacrylic acid, acrylonitrile, styrene), an "associative monomer", and an optional crosslinking monomer. The associative monomer comprises an ethylenically unsaturated polymerizable end group, a non-ionic hydrophilic midsection that is terminated by a hydrophobic end group. The non-ionic hydrophilic midsection comprises a polyoxyalkylene group, e.g., polyethylene oxide, polypropylene oxide, or mixtures of polyethylene oxide/polypropylene oxide segments. The terminal hydrophobic end group is typically a $C_8$-$C_{40}$ aliphatic moiety. Exemplary aliphatic moieties are selected from linear and branched alkyl substituents, linear and branched alkenyl substituents, carbocyclic substituents, aryl substituents, aralkyl substituents, arylalkyl substituents, and alkylaryl substituents. In one aspect associative monomers can be prepared by the condensation (e.g., esterification or etherification) of a polyethoxylated and/or polypropoxylated aliphatic alcohol (typically containing a branched or unbranched $C_8$-$C_{40}$ aliphatic moiety) with an ethylenically unsaturated monomer containing a carboxylic acid group (e.g., acrylic acid, methacrylic acid), an unsaturated cyclic anhydride monomer (e.g., maleic anhydride, itaconic anhydride, citraconic anhydride), a monoethylenically unsaturated monoisocyanate (e.g., α,α-dimethyl-m-isopropenyl benzyl isocyanate) or an ethylenically unsaturated monomer containing a hydroxyl group (e.g., vinyl alcohol, allyl alcohol). Polyethoxylated and/or polypropoxylated aliphatic alcohols are ethylene oxide and/or propylene oxide adducts of a monoalcohol containing the $C_8$-$C_{40}$ aliphatic moiety. Non-limiting examples of alcohols containing a $C_8$-$C_{40}$ aliphatic moiety are capryl alcohol, isooctyl alcohol (2-ethyl hexanol), pelargonic alcohol (1-nonanol), decyl alcohol, lauryl alcohol, myristyl alcohol, cetyl alcohol, cetearyl alcohol (mixture of $C_{16}$-$C_{18}$ monoalcohols), stearyl alcohol, isostearyl alcohol, elaidyl alcohol, oleyl alcohol, arachidyl alcohol, behenyl alcohol, lignoceryl alcohol, ceryl alcohol, montanyl alcohol, melissyl alcohol, lacceryl alcohol, geddyl alcohol, and $C_2$-$C_{20}$ alkyl substituted phenols (e.g., nonyl phenol), and the like.

Exemplary HASE polymers are disclosed in U.S. Pat. Nos. 3,657,175; 4,384,096; 4,464,524; 4,801,671; and 5,292,843 which are herein incorporated by reference. In addition, an extensive review of HASE polymers is found in Gregory D. Shay, Chapter 25, "Alkali-Swellable and Alkali-Soluble Thickener Technology A Review", Polymers in Aqueous Media—Performance Through Association, Advances in Chemistry Series 223, J. Edward Glass (ed.), ACS, pp. 457-494, Division Polymeric Materials, Washington, D.C. (1989), the relevant disclosures of which are incorporated herein by reference. The HASE polymers are commercially available from Rohm & Haas under the trade designations Aculyn® 22 (INCI Name: Acrylates/Steareth-20 Methacrylate Copolymer), Aculyn® 44 (INCI Name: PEG-150/Decyl Alcohol/SMDI Copolymer), Aculyn 46® (INCI Name: PEG-150/Stearyl Alcohol/SMDI Copolymer), and Aculyn® 88 (INCI Name: Acrylates/Steareth-20 Methacrylate Crosspolymer).

Another class of synthetic and semi-synthetic rheology modifiers suitable for use in the present invention includes cationically modified acrylic polymers and copolymers and cationically modified cellulose ethers. The acrylic polymers and copolymers and cellulose ethers are cationically modified via quaternization. For the acrylic polymers and copolymers, quaternization can occur by polymerizing a quaternized monomer into the acrylic polymer backbone or by post functionalizing the acrylic polymer with a quaternizing agent. An exemplary quaternary acrylic polymer is designated under INCI nomenclature as Polyquaternium-37 and is commercially available under the trade names Synthalen CR21 and Synthalen CN, from 3V Inc. The quaternized celluloses are prepared by post functionalizing the desired cellulosic backbone (e.g., hydroxyethyl cellulose) with a quaternizing agent such as a quaternary ammonium salt (e.g., diallyldimethyl ammonium chloride, trimethyl ammonium chloride substituted epoxide). Exemplary quaternary cellulosic polymers are designated under the INCI names Polyquaternium-4, Polyquaternium-10, and Polyquaternium-67.

In another embodiment, acid swellable associative polymers are useful rheology modifiers. Such polymers generally have cationic and associative characteristics. These polymers are free radical addition polymers polymerized from a monomer mixture comprising an acid sensitive amino substituted hydrophilic monomer (e.g., dialkylamino alkyl (meth)acrylates or (meth)acrylamides), an associative monomer (defined hereinabove), a lower alkyl (meth)acrylate or other free radically polymerizable comonomers selected from hydroxyalkyl esters of (meth)acrylic acid, vinyl and/or allyl ethers of polyethylene glycol, vinyl and/or allyl ethers of polypropylene glycol, vinyl and/or allyl ethers of polyethylene glycol/polypropylene glycol, polyethylene glycol esters of (meth)acrylic acid, polypropylene glycol esters of (meth)acrylic acid, polyethylene glycol/polypropylene glycol esters of (meth)acrylic acid), and combinations thereof. These polymers can optionally be crosslinked. By acid sensitive is meant that the amino substituent becomes cationic at low pH values, typically ranging from about 0.5 to about 6.5. Exemplary acid swellable associative polymers are commercially available under the trade name Structure® Plus (INCI Name: Acrylates/Aminoacrylates/C10-C30 Alkyl PEG-20 Itaconate) from National Starch and Chemical Company, and Carbopol® Aqua CC (INCI Name: Polyacrylates-1 Crosspolymer) from Lubrizol Advanced Materials, Inc. In one aspect the acid swellable polymer is a copolymer of one or more $C_1$-$C_5$ alkyl esters of (meth)acrylic acid, $C_1$-$C_4$ dialkylamino $C_1$-$C_6$ alkyl methacrylate, PEG/PPG-30/5 allyl ether, PEG 20-25 $C_{10}$-$C_{30}$ alkyl ether methacrylate, hydroxy $C_2$-$C_6$ alkyl methacrylate crosslinked with ethylene glycol dimethacrylate. Other useful acid swellable associative polymers are disclosed in U.S. Pat. No. 7,378,479, the disclosure of which is herein incorporated by reference.

Hydrophobically modified alkoxylated methyl glucoside, such as, for example, PEG-120 Methyl Glucose Dioleate, PEG-120 Methyl Glucose Trioleate, and PEG-20 Methyl Glucose Sesquistearate, available from Lubrizol Advanced Materials, Inc., under the trade names, Glucamate® DOE-120, Glucamate™ LT, and Glucamate™ SSE-20, respectively, are also suitable rheology modifiers.

The rheology modifiers set forth above, when employed, can be used alone or in combination and typically are used in an amount ranging from about 0.1 wt. % to about 5 wt. % in one aspect, from about 0.3 wt. % to about 3 wt. % in another aspect, and from about 0.5 wt. % to about 2 wt. % in further aspect, based on the total weight of the personal care, home care, health care, and institutional care compositions of the present invention.

Exemplary emulsifiers include but are not limited to $C_{12}$-$C_{18}$ fatty alcohols; alkoxylated $C_{12}$-$C_{18}$ fatty alcohols $C_{12}$-$C_{18}$ fatty acids, and alkoxylated $C_{12}$-$C_{18}$ fatty acids, the alkoxylates each having 10 to 30 units of ethylene oxide, propylene oxide, and combinations of ethylene oxide/propylene oxide; $C_8$-$C_{22}$ alkyl mono- and oligoglycosides; ethoxylated sterols; partial esters of polyglycerols; esters and partial esters of polyols having 2 to 6 carbon atoms and saturated and unsaturated fatty acids having 12 to 30 carbon atoms; partial esters of polyglycerols; and organosiloxanes; and combinations thereof.

The fatty alcohols, acids and alkoxylated fatty alcohols and fatty acids are as described in the emollient description above. In one aspect of the invention the fatty alcohols and fatty acids each are ethoxylated with 10 to 30 units of ethylene oxide.

The $C_8$-$C_{22}$ alkyl mono- and oligoglycoside emulsifiers are prepared by reacting glucose or an oligosaccharide with primary fatty alcohols having 8 to 22 carbon atoms. Products which are obtainable under the trademark Plantacare® comprise a glucosidically bonded $C_8$-$C_{16}$ alkyl group on an oligoglucoside residue whose average degree of oligomerization is 1 to 2. Exemplary alkyl glucosides and oligoglycosides are selected from octyl glucoside, decyl glucoside, lauryl glucoside, palmityl glucoside, isostearyl glucoside, stearyl glucoside, arachidyl glucoside and behenyl glucoside, and mixtures thereof.

Exemplary ethoxylated sterols include ethoxylated vegetable oil sterols such as, for example, soya sterols. The degree of ethoxylation is greater than about 5 in one aspect, and at least about 10 in another aspect. Suitable ethoxylated sterols are PEG-10 Soy Sterol, PEG-16 Soy Sterol and PEG-25 Soy Sterol.

The partial esters of polyglycerols have 2 to 10 glycerol units and are esterified with 1 to 4 saturated or unsaturated, linear or branched, optionally hydroxylated $C_8$-$C_{30}$ fatty acid residues. Representative partial esters of polyglycerols include diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate, decaglycerol trihydroxystearate, and mixtures thereof.

The saturated $C_{12}$-$C_{30}$ fatty alcohol emulsifiers are as described in the emollient description set forth above. In one aspect of the invention, the fatty alcohol emulsifier is selected from but not limited to cetyl alcohol, stearyl alcohol, arachidyl alcohol, behenyl alcohol and lanolin alcohol or mixtures of these alcohols, and as are obtainable in the hydrogenation of unsaturated vegetable oil and animal fatty acids.

Emulsifiers based on the esters and partial esters of polyols having 2 to 6 carbon atoms and linear saturated and unsaturated fatty acids having 12 to 30 carbon atoms are, for example, the monoesters and diesters of glycerol or ethylene glycol or the monoesters of propylene glycol with saturated and unsaturated $C_{12}$ to $C_{30}$ fatty acids.

The partially esterified polyglycerol emulsifiers include 2 to about 10 glycerol units and esterified with 1 to 5 saturated or unsaturated, linear or branched, optionally hydroxylated $C_8$ to $C_{30}$ fatty acid residues.

The organosiloxane emulsifiers are polymeric emulsifiers that contain at least one hydrophobic portion and at least one hydrophilic portion. The polymer backbone contains repeating siloxy units that can have cyclic, linear or branched repeating units, e.g. di($C_1$-$C_5$)alkylsiloxy units, typically dimethylsiloxy units.

The hydrophilic portion of the organosiloxane is generally achieved by substitution onto the polymeric backbone of a residue that confers hydrophilic properties to a portion of the molecule. The hydrophilic residue may be substituted on a terminus of the polymeric organosiloxane, or on any one or more repeating units of the polymer. Generally, the hydrophilic residue is derived from ethylene oxide units that are grafted onto the polymer backbone. In general, the repeating dimethylsiloxy units of modified polydimethylsiloxane emulsifiers are hydrophobic in nature due to the methyl groups, and confer the hydrophobicity properties to the molecule. In addition, longer chain alkyl residues, hydroxy terminated polypropyleneoxy residues, hydroxy terminated polyether residues comprising a combination of ethylene oxide and propylene oxide residues, and/or other types of residues can be substituted onto the siloxy backbone to confer additional emulsification properties to the backbone. Polyether substituted organosiloxane emulsifiers are known as dimethicone copolyols and are widely commercially available. The dimethicone polyols can be random or block copolymers. A generally useful class of dimethicone polyols is block copolymers having blocks of polydimethylsiloxane and blocks of polyalkylene oxide, such as blocks of polyethylene oxide, polypropylene oxide, or both.

Dimethicone copolyols are disclosed in U.S. Pat. Nos. 5,136,063 and 5,180,843, the disclosures of which are incorporated herein by reference. In addition, dimethicone copolyols are commercially available under the Silsoft® and Silwet® brand names from the General Electric Company (GE-OSi). Specific product designations include but are not limited to Silsoft 305, 430, 475, 810, 895, Silwet L 7604 (GE-OSi); Dow Corning® 5103 and 5329 from Dow Corning Corporation; and Abil® dimethicone copolyols, such as, for example WE 09, WS 08, EM 90 and EM 97 from Evonik Goldschmidt Corporation; and Silsense™ dimethicone copolyols, such as Silsense Copolyol-1 and Silsense Copolyol-7, available from Lubrizol Advanced Materials, Inc.

Blends of dimethicone copolyols in cyclomethicone fluids are also useful emulsifiers in the present invention. An exemplary dimethicone/cyclomethicone blend is commercially available as Dow Corning® 5225 C and is a 10 wt. % dispersion of PEG/PPG-18/18 Dimethicone in cyclopentasiloxane fluid available from Dow Corning Corporation.

In one aspect of the invention the emulsifier can be present in an amount ranging from about 0.5 wt. % to about 12 wt. %, from about 1 wt. % to about 15 wt. % in another aspect, and from about 5 wt. % to about 10 wt. % in a further aspect, based on the total weight of the personal care, home care, health care, and institutional care composition.

Suitable emollients include but are not limited to an emollient selected from silicone fluids (e.g., volatile silicone oils and non-volatile silicone oils); mineral oils; petrolatums; vegetable oils; fish oils; fatty alcohols; fatty acids; fatty acid and fatty alcohol esters; alkoxylated fatty alcohols; alkoxylated fatty acid esters; benzoate esters; Guerbet esters; alkyl ether derivatives of polyethylene glycols, such as, for example methoxypolyethylene glycol (MPEG); and polyalkylene glycols; lanolin and lanolin derivatives; and the like. The emollient can be used alone or in combination with one or more emollients of the present invention.

Volatile silicone oils include cyclic and linear polydimethylsiloxanes, low molecular weight organo-functional silicones, and the like. Cyclic volatile silicones (cyclomethicones) typically contain about 3 to about 7 silicon atoms, alternating with oxygen atoms, in a cyclic ring structure. Each silicon atom is typically substituted with two alkyl groups, such as, for example, methyl groups. Volatile linear polydimethylsiloxanes (dimethicones) typically contain about 2 to about 9 silicon atoms, alternating with oxygen atoms in a linear arrangement. Each silicon atom is also substituted with two alkyl groups (the terminal silicon atoms are substituted with three alkyl groups), such as, for example, methyl groups. The linear volatile silicones typically have viscosities of less than about 5 cP at 25° C., while the cyclic volatile silicones typically have viscosities of less than about 10 cP at 25° C. "Volatile" means that the silicone has a measurable vapor pressure, or a vapor pressure of at least 2 mm of Hg at 20° C. Non-volatile silicones have a vapor pressure of less than 2 mm Hg at 20° C. A description of volatile silicones is found in Todd and Byers, "Volatile Silicone Fluids for Cosmetic Formulations", Cosmetics and Toiletries, Vol. 91, pp. 29-32 (January 1976), and in Kasprzak, "Volatile Silicones", Soap/Cosmetics/Chemical Specialties, pp. 40-43 (December 1986), each incorporated herein by reference.

Exemplary volatile cyclomethicones are D4 cyclomethicone (octamethylcyclotetrasiloxane), D5 cyclomethicone (decamethylcyclopentasiloxane), D6 cyclomethicone, and blends thereof (e.g., D4/D5 and D5/D6). Volatile cyclomethicones and cyclomethicone blends are commercially available from G.E. Silicones as SF1173, SF1202, SF1256, and SF1258, Dow Corning Corporation as Dow Corning® 244, 245, 246, 345, and 1401 Fluids. Blends of volatile cyclomethicones and volatile linear dimethicones are also contemplated.

Exemplary volatile linear dimethicones include hexamethyldisiloxane, octamethyltrisiloxane, decamethyltetrasiloxane, dodecamethylpentasiloxane and blends thereof. Volatile linear dimethicones and dimethicone blends are commercially available from Dow Corning Corporation as Dow Corning 200® Fluid (e.g., product designations 0.65 CST, 1 CST, 1.5 CST, and 2 CST) and Dow Corning® 2-1184 Fluid.

Exemplary volatile low molecular weight organo-functional silicones include phenyl trimethicone, caprylyl trimethicone, caprylyl methicone, and hexyl methicone, and blends thereof. Low molecular weight organo-functional silicones are commercially available from Clariant under the trade name Silcare® 41M10, Silcare® 31M60, Silcare® 41M10, and Silcare® 41M15.

The non-volatile silicone oils useful as emollients in the present invention are linear and typically have viscosities of from about 10 cP to about 100,000 cP at 25° C. They typically contain above about 10 dialkyl/diaryl or monoalkyl/monoaryl substituted silicon atoms, alternating with oxygen atoms in a linear arrangement. They include polyalkylsiloxane, polyarylsiloxane, and polyalkylarylsiloxane polymers. Exemplary non-volatile silicone oils include the polydimethylsiloxanes (dimethicones), polydiethylsiloxanes, polymethylphenylsiloxanes, and the like. In one aspect of the invention, the non-volatile silicone oil is selected from a non-volatile polydimethylsiloxane having a viscosity range from about 10 cP to about 100,000 cP at 25° C. Non-volatile dimethicones are commercially available from Dow Corning Corporation as Dow Corning 200® Fluid (product designations 10 CST through 10,000 CST).

Mineral oils and petrolatums include cosmetic, USP and NF grades and are commercially available from Penreco under the Drakeol® and Penreco® trade names. Mineral oil includes hexadecane and paraffin oil.

Exemplary vegetable oils suitable an emollient component in the present invention include but are not limited to peanut oil, sesame oil, avocado oil, coconut oil, cocoa butter, almond oil, safflower oil, corn oil, cotton seed oil, sesame seed oil, walnut oil, castor oil, olive oil, jojoba oil, palm oil, palm kernel oil, soybean oil, wheat germ oil, linseed oil, sunflower seed oil; and the mono-, di-, and triglycerides thereof. Exemplary mono-, di- and triglycerides are, for example, caprylic triglyceride, capric triglyceride, caprylic/capric triglyceride, and caprylic/capric/lauric triglyceride, caprylic/capric/stearic triglyceride, and caprylic/capric/linoleic triglyceride.

Ethoxylated mono- and diglycerides are also suitable as an emollient component of the present invention, such as, for example, PEG-8 Caprylic/Capric Glycerides.

Suitable fatty alcohol emollients include but are not limited to fatty alcohols containing 8 to 30 carbon atoms. Exemplary fatty alcohols include capryl alcohol, pelargonic alcohol, capric alcohol, lauryl alcohol, myristyl alcohol, cetyl alcohol, isocetyl alcohol, stearyl alcohol, isostearyl alcohol, cetearyl alcohol, oleyl alcohol, ricinoleyl alcohol, arachidyl alcohol, icocenyl alcohol, behenyl alcohol, and mixtures thereof.

Suitable fatty acid emollients include but are not limited to fatty acids containing 10 to 30 carbon atoms. Exemplary fatty acids are selected from capric acid, lauric acid, myristic acid, palmitic acid, stearic acid, oleic acid, linoleic acid, arachidic acid, behenic acid, and mixtures thereof.

Suitable fatty acid and fatty alcohol ester emollients include but are not limited to hexyl laurate, decyl oleate, isopropyl stearate, isopropyl isostearate, butyl stearate, octyl stearate, cetyl stearate, myristyl myristate, octyldodecyl stearoylstearate, octylhydroxystearate, diisopropyl adipate, isopropyl myristate, isopropyl palmitate, ethyl hexyl palmitate, isodecyl oleate, isodecyl neopentanoate, diisopropyl sebacate, isostearyl lactate, lauryl lactate, diethyl hexyl maleate, PPG-14 butyl ether and PPG-2 myristyl ether propionate, cetearyl octanoate, and mixtures thereof.

Alkoxylated fatty alcohols are ethers formed from the reaction of a fatty alcohol with an alkylene oxide, generally ethylene oxide or propylene oxide. Suitable ethoxylated fatty alcohols are adducts of fatty alcohols and polyethylene oxide. In one aspect of the invention, the ethoxylated fatty alcohols can be represented by the formula R—$(OCH_2CH_2)_n$—OH, wherein R represents the aliphatic residue of the parent fatty alcohol and n represents the number of molecules of ethylene oxide. In another aspect of the invention, R is derived from a fatty alcohol containing 8 to 30 carbon atoms. In one aspect, n is an integer ranging from 2 to 50, 3 to 25 in another aspect, and 3 to 10 in a further aspect. In a still further aspect, R is derived from a fatty alcohol emollient set forth above. Exemplary ethoxylated fatty alcohols are but are not limited to capryl alcohol ethoxylate, lauryl alcohol ethoxylate, myristyl alcohol ethoxylate, cetyl alcohol ethoxylate, stearyl alcohol ethoxylate, cetearyl alcohol ethoxylate oleyl alcohol ethoxylate, and, behenyl alcohol ethoxylate, wherein the number of ethylene oxide units in each of the foregoing ethoxylates can range from 2 and above in one aspect, and from 2 to about 150 in another aspect. It is to be recognized that the propoxylated adducts of the foregoing fatty alcohols and mixed ethoxylated/propoxylated adducts of the foregoing fatty alcohols are also contemplated within the scope of the invention. The ethylene oxide and propylene oxide units of the ethoxylated/propoxylated fatty alcohols can be arranged in random or in blocky order.

More specific examples of ethoxylated alcohols are but are not limited to Beheneth 5-30 (the 5-30 meaning the range of repeating ethylene oxide units), Ceteareth 2-100, Ceteth 1-45, Cetoleth 24-25, Choleth 10-24, Coceth 3-10, C9-11 pareth 3-8, C11-15 pareth 5-40, C11-21 Pareth 3-10, C12-13 pareth 3-15, Deceth 4-6, Dodoxynol 5-12, Glycereth 7-26, Isoceteth 10-30, Isodeceth 4-6, Isolaureth 3-6, isosteareth 3-50, Laneth 5-75, Laureth 1-40, Nonoxynol 1-120, Nonylnonoxynol 5-150, Octoxynol 3-70, Oleth 2-50, PEG 4-350, Steareth 2-100, and Trideceth 2-10.

Specific examples of propoxylated alcohols are but are not limited to PPG-10 Cetyl Ether, PPG-20 Cetyl Ether, PPG-28 Cetyl Ether, PPG-30 Cetyl Ether, PPG-50 Cetyl Ether, PPG-2 Lanolin Alcohol Ether, PPG-5 Lanolin Alcohol Ether, PPG-10 Lanolin Alcohol Ether, PPG-20 Lanolin Alcohol Ether, PPG-30 Lanolin Alcohol Ether, PPG-4 Lauryl Ether, PPG-7 Lauryl Ether, PPG-10 Oleyl Ether, PPG-20 Oleyl Ether, PPG-23 Oleyl Ether, PPG-30 Oleyl Ether, PPG-37 Oleyl Ether, PPG-50 Oleyl Ether, PPG-11 Stearyl Ether, PPG-15 Stearyl Ether, PPG-2 Lanolin Ether, PPG-5 Lanolin Ether, PPG-10 Lanolin Ether, PPG-20 Lanolin Ether, PPG-30 Lanolin Ether, and PPG-1 Myristyl Ether.

Specific examples of ethoxylated/propoxylated alcohols are but are not limited to PPG-1 Beheneth-15, PPG-12 Capryleth-18, PPG-2-Ceteareth-9, PPG-4-Ceteareth-12, PPG-10-Ceteareth-20, PPG-1-Ceteth-1, PPG-1-Ceteth-5 PPG-1-Ceteth-10, PPG-1-Ceteth-20, PPG-2-Ceteth-1, PPG-2-Ceteth-5, PPG-2-Ceteth-10, PPG-2-Ceteth-20, PPG-4-Ceteth-1, PPG-4-Ceteth-5, PPG-4-Ceteth-10, PPG-4-Ceteth-20, PPG-5-Ceteth-20, PPG-8-Ceteth-1, PPG-8-Ceteth-2, PPG-8-Ceteth-5, PPG-8-Ceteth-10, PPG-8-Ceteth-20, PPG-2 C12-13 Pareth-8, PPG-2 C12-15 Pareth-6, PPG-4 C13-15 Pareth-15, PPG-5 C9-15 Pareth-6, PPG-6 C9-11 Pareth-5, PPG-6 C12-15 Pareth-12, PPG-6 C12-18 Pareth-11, PPG-3 C12-14 Sec-Pareth-7, PPG-4 C12-14 Sec-Pareth-5, PPG-5 C12-14 Sec-Pareth-7, PPG-5 C12-14 Sec-Pareth-9, PPG-1-Deceth-6, PPG-2-Deceth-3, PPG-2-Deceth-5, PPG-2-Deceth-7, PPG-2-Deceth-10, PPG-2-Deceth-12, PPG-2-Deceth-15, PPG-2-Deceth-20, PPG-2-Deceth-30, PPG-2-Deceth-40, PPG-2-Deceth-50, PPG-2-Deceth-60, PPG-4-Deceth-4, PPG-4-Deceth-6, PPG-6-Deceth-4, PPG-6-Deceth-9, PPG-8-Deceth-6, PPG-14-Deceth-6, PPG-6-Decyltetradeceth-12, PPG-6-Decyltetradeceth-20, PPG-6-Decyltetradeceth-30, PPG-13-Decyltetradeceth-24, PPG-20-Decyltetradeceth-10, PPG-2-Isodeceth-4, PPG-2-Isodeceth-6, PPG-2-Isodeceth-8, PPG-2-Isodeceth-9, PPG-2-Isodeceth-10, PPG-2-Isodeceth-12, PPG-2-Isodeceth-18, PPG-2-Isodeceth-25, PPG-4 Isodeceth-10, PPG-12-Laneth-50, PPG-2-Laureth-5, PPG-2-Laureth-8, PPG-2-Laureth-12, PPG-3-Laureth-8, PPG-3-Laureth-9, PPG-3-Laureth-10, PPG-3-Laureth-12, PPG-4 Laureth-2, PPG-4 Laureth-5, PPG-4 Laureth-7, PPG-4-Laureth-15, PPG-5-Laureth-5, PPG-6-Laureth-3, PPG-25-Laureth-25, PPG-7 Lauryl Ether, PPG-3-Myreth-3, PPG-3-Myreth-11, PPG-20-PEG-20 Hydrogenated Lanolin, PPG-2-PEG-11 Hydrogenated Lauryl Alcohol Ether, PPG-12-PEG-50 Lanolin, PPG-12-PEG-65 Lanolin Oil, PPG-40-PEG-60 Lanolin Oil, PPG-1-PEG-9 Lauryl Glycol Ether, PPG-3-PEG-6 Oleyl Ether, PPG-23-Steareth-34, PPG-30 Steareth-4, PPG-34-Steareth-3, PPG-38 Steareth-6, PPG-1 Trideceth-6, PPG-4 Trideceth-6, and PPG-6 Trideceth-8.

Alkoxylated fatty acids are formed when a fatty acid is reacted with an alkylene oxide or with a pre-formed polymeric ether. The resulting product may be a monoester, diester, or mixture thereof. Suitable ethoxylated fatty acid ester emollients suitable for use in the present invention are products of the addition of ethylene oxide to fatty acids. The product is a polyethylene oxide ester of a fatty acid. In one aspect of the invention, the ethoxylated fatty acid esters can be represented by the formula $R—C(O)O(CH_2CH_2O)_n—H$, wherein R represents the aliphatic residue of a fatty acid and n represents the number of molecules of ethylene oxide. In another aspect, n is an integer ranging from 2 to 50, 3 to 25 in another aspect, and 3 to 10 in a further aspect. In still another aspect of the invention, R is derived from a fatty acid containing 8 to 24 carbon atoms. In a still further aspect, R is derived from a fatty acid emollient set forth above. It is to be recognized that propoxylated and ethoxylated/propoxylated products of the foregoing fatty acids are also contemplated within the scope of the invention. Exemplary alkoxylated fatty acid esters include but are not limited to capric acid ethoxylate, lauric acid ethoxylate, myristic acid ethoxylate, stearic acid ethoxylate, oleic acid ethoxylate, coconut fatty acid ethoxylate, and polyethylene glycol 400 propoxylated monolaurate, wherein the number of ethylene oxide units in each of the foregoing ethoxylates can range from 2 and above in one aspect, and from 2 to about 50 in another aspect. More specific examples of ethoxylated fatty acids are PEG-8 distearate (the 8 meaning the number of repeating ethylene oxide units), PEG-8 behenate, PEG-8 caprate, PEG-8 caprylate, PEG-8 caprylate/caprate, PEG cocoates (PEG without a number designation meaning that the number of ethylene oxide units ranges from 2 to 50), PEG-15 dicocoate, PEG-2 diisononanoate, PEG-8 diisostearate, PEG dilaurates, PEG-dioleates PEG-distearates, PEG Ditallates, PEG-isostearates, PEG-jojoba acids, PEG-laurates, PEG-linolenates, PEG-myristates, PEG-oleates, PEG-palmitates, PEG-ricinoleates, PEG-stearates, PEG-tallates, and the like.

Guerbet ester emollients are formed from the esterification reaction of a Guerbet alcohol with a carboxylic acid. Guerbet ester emollients are commercially available from the Noveon Consumer Specialties Division of Lubrizol Advanced Materials, Inc. under product designations G-20, G-36, G-38, and G-66.

Lanolin and lanolin derivatives are selected from lanolin, lanolin wax, lanolin oil, lanolin alcohols, lanolin fatty acids, alkoxylated lanolin, isopropyl lanolate, acetylated lanolin alcohols, and combinations thereof. Lanolin and lanolin derivatives are commercially available from the Noveon Consumer Specialties Division of Lubrizol Advanced Materials, Inc. under the trade names Lanolin LP 108 USP, Lanolin USP AAA, Acetulan™, Ceralan™, Lanocerin™, Lanogel™ (product designations 21 and 41), Lanogene™, Modulan™, Ohlan™, Solulan™ (product designations 16, 75, L-575, 98, and C-24), Vilvanolin™ (product designations C, CAB, L-101, and P).

The emollient(s) can be utilized in an amount ranging from about 0.5 wt. % to about 30 wt. % by weight of the total personal care composition in one aspect 0.1 wt. % to 25 wt. % in another aspect, and 5 wt. % to 20 wt. % in a further aspect. While emollients are generally employed in personal care compositions, they can be employed in home care, health care, and institutional care compositions in the same wt. ratios as set forth for personal care compositions so long as they effect a desired physical attribute (e.g., humectant properties) in such compositions.

Surfactants can be employed as cleansing agents, emulsifying agents, stabilizers, foam boosters, structurants, hydrotropes and suspending agents. While amounts of the surfactant if employed can vary widely, the amounts which are often utilized generally range from about 1 wt. % to about 80 wt. % of the in one aspect, from about 5 wt. % to about 65 wt. % in another aspect, from about 6 wt. % to about 30 wt. % in a further aspect, and from about 8 wt. % to about 20 wt. % in a still further aspect of the invention, based upon the total weight of the personal care, health care, home care and institutional care compositions of the present invention. The surfactant can be selected from any class of surfactants, i.e., anionic surfactants, cationic surfactants, nonionic surfactants, amphoteric surfactants, and mixtures thereof. The term "amphoteric surfactant" as used herein includes zwitterionic surfactants. In-depth discussions of the various classes of surfactants are contained in the Cosmetics & Toletries® C&T Ingredient Resource Series, "Surfactant Encyclopedia", 2nd Edition, Rieger (ed), Allured Publishing Corporation (1996); Schwartz, at al., Surface Active Agents, Their Chemistry and Technology, published 1949; and Surface Active Agents and Detergents, Volume II, published 1958, Interscience Publishers; each incorporated herein by reference.

Non-limiting examples of anionic surfactants include mono-basic salts of acylglutamates that are slightly acidic in aqueous solution, such as sodium acylglutamate and sodium hydrogenated tallow glutamate; salts of acyl-hydrolyzed protein, such as potassium, palmitoyl hydrolyzed milk protein, sodium cocoyl hydrolyzed soy protein, and TEA-abietoyl hydrolyzed collagen; salts of acyl sarcosinates, such as ammonium myristoyl sarcosine, sodium cocoyl sarcosinate, and TEA-lauroyl sarcosinate; salts of sodium methyl acyltaurates, such as sodium lauroyl taurate, sodium methyl oleyl taurate and sodium methyl cocoyl taurate; alkanoic acids and alkanoates, such as fatty acids derived from animal and vegetable glycerides that form water-soluble soaps and water-insoluble emulsifying soaps, including sodium stearate, ammonium stearate, aluminum stearate, and zinc undecylenate; ester carboxylic acids, such as dinonoxynol-9-citrate; salts of acyl lactylates such as calcium stearoyl lactylate and laureth-6 citrate; ethercarboxylic acids derived from ethyoxylated alcohols or phenols having varying lengths of polyoxyethylene chains, such as nonoxynol-8 carboxylic acid, and sodium trideceth-13 carboxylate; mono- and di-esters of phosphoric acid and their salts, such as phospholipids, dilaureth-4-phosphate, DEA-oleth-10 phosphate and triethanolamine lauryl phosphate; salts of acylisethionate, such as sodium cocoyl isethionate; alkylarylbenzene sulfonates, such as alpha-olefin sulfonates (AOS) and alkali metal, alkaline earth metal, and alkanolamine salts thereof, and sodium dodecylbenzene sulfonate; alkyl sulfonates, such as sodium $C_{12}$ to $C_{14}$ olefin sulfonate, sodium $C_{14}$ to $C_{16}$ olefin sulfonate, sodium cocomonoglyceride sulfonate, sodium $C_{12}$ to $C_{15}$ pareth-15 sulfonate, and sodium lauryl sulfoacetate; sulfosuccinates, such as mono- and di-esters of sulfosuccinic acid, salts thereof and alkoxylated alkyl and alkylamido derivatives thereof, such as di-$C_4$ to $C_{10}$ alkyl sodium sulfosuccinate, disodium laureth sulfosuccinate, disodium oleamido MEA-sulfosuccinate, and disodium $C_{12}$ to $C_{15}$ pareth sulfosuccinate; alkyl ether sulfates, such as sodium and ammonium lauryl ether sulfate (having about 1 to about 12 moles ethylene oxide), e.g., sodium laureth sulfate; alkyl sulfates, such as sodium, ammonium and triethanolamine salts of $C_{12}$ to $C_{18}$ alkylsulfates, sodium $C_{12}$ to $C_{14}$ olefin sulfates, sodium laureth-6 carboxylate, sodium $C_{12}$ to $C_{18}$ pareth sulfate, and the like.

Cationic surfactants can have a hydrophobe that carries a positive charge such as, for example, alkylamines, alkyl imidazolines, ethoxylated amines, and quaternary ammonium compounds. Cationic surfactants used in cosmetics are preferably N-derivatives and the neutralizing anion may be inorganic or organic. Among the cationic surfactant materials useful herein are quaternary ammonium compounds corresponding to the general formula: $(R^{14}R^{15}R^{16}R^{17}N^+)$ E$^-$, wherein each of $R^{14}$, $R^{15}$, $R^{16}$, and $R^{17}$ are independently selected from an aliphatic group having from 1 to about 30 carbon atoms, or an aromatic, alkoxy, polyoxyalkylene, alkylamido, hydroxyalkyl, aryl or alkylaryl group having 1 to about 22 carbon atoms in the alkyl chain; and E$^-$ is a salt-forming anion such as those selected from halogen, (e.g. chloride, bromide), acetate, citrate, lactate, glycolate, phosphate, nitrate, sulfate, and alkylsulfate. The aliphatic groups can contain, in addition to carbon and hydrogen atoms, ether linkages, ester linkages, and other groups such as amino groups. The longer chain aliphatic groups, e.g., those of about 12 carbons, or higher, can be saturated or unsaturated.

Alkylamines can be salts of primary, secondary and tertiary fatty $C_{12}$ to $C_{22}$ alkylamines, substituted or unsubstituted, and substances sometimes referred to as "amidoamines". Non-limiting examples of alkyl amines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane). Non-limiting examples of amidoamines and salts thereof include stearamido propyl dimethyl amine, stearamidopropyl dimethylamine citrate, palmitamidopropyl diethylamine, and cocamidopropyl dimethylamine lactate. Other cationic surfactants include distearyldimonium chloride, dicetyldimonium chloride, guar hydroxypropyltrimonium chloride, and the like. At low pH, amine oxides may protonate and behave similarly to N-alkyl amines.

Non-limiting examples of alkyl imidazolines include alkyl hydroxyethyl imidazoline, such as stearyl hydroxyethyl imidazoline, coco hydroxyethyl imidazoline, ethyl hydroxymethyl oleyl oxazoline, and the like. Non-limiting examples of ethyoxylated amines include PEG-cocopolyamine, PEG-15 tallow amine, quaternium-52, and the like.

Quaternary ammonium compounds are monomeric or polymeric materials containing at least one nitrogen atom that is linked covalently to four alkyl and/or aryl substituents, and the nitrogen atom remains positively charged regardless of the environmental pH. Quaternary ammonium compounds comprise a large number of substances that are used extensively as surfactants, conditioners, antistatic agents, and antimicrobial agents and include, alkylbenzyldimethyl ammonium salts, alkyl betaines, heterocyclic ammonium salts, and tetraalkylammonium salts. Long-chain (fatty) alkylbenzyldimethyl ammonium salts are preferred as conditioners, as antistatic agents, and as fabric softeners, discussed in more detail below. Other quaternary ammonium compounds include quaternary ammonium silicones. An extensive listing of quaternary ammonium compounds suitable for use herein and their functions appears in the INCI Dictionary, generally, and in Vol. 2, Section 4 of the Seventh Edition, both of which are incorporated herein by reference.

Non-limiting examples of alkylbenzyldimethylammonium salts include stearalkonium chloride, benzalkonium chloride, quaternium-63, olealkonium chloride, didecyldimonium chloride, and the like. Alkyl betaine compounds include alkylamidopropyl betaine, alkylamidopropyl hydroxysultaine, and sodium alkylamido propyl hydroxyphostaine. Non-limiting examples of alkyl betaine compounds include oleyl betaine, coco-betaine, cocamidopropylbetaine, coco-hydroxy sultaine, sultaine, coco/oleamidopropyl betaine, coco-sultaine, cocoamidopropylhydroxy sultaine, and sodium lauramidopropyl hydroxyphostaine. Heterocyclic ammonium salts include alkylethyl morpholinium ethosulfate, isostearyl ethylimidonium ethosulfate, and alkylpyridinium chlorides, and are generally used as emulsifying agents. Non-limiting examples of heterocyclic ammonium salts include cetylpyridinium chloride, isostearylethylimidonium ethosulfate, and the like. Non-limiting examples of tetraalkylammonium salts include cocamidopropyl ethyldimonium ethosulfate, hydroxyethyl cetyldimonium chloride, quaternium-18, and cocodimonium hyroxypropyl hydrolyzed protein, such as hair keratin, and the like.

Suitable amphoteric or zwitterionic surfactants for use in the present compositions include those broadly described as derivatives of aliphatic quaternary ammonium, phosphonium, and sulfonium compounds, wherein which the aliphatic radicals can be straight chain or branched, and wherein one of the aliphatic substituents contains about 8 to about 30 carbon atoms and another substituent contains an anionic water-solubilizing group, such as carboxy, sulfonate, sulfate, phosphate, phosphonate, and the like. Classes of zwitterionics include alkylamino sulfonates, alkyl betaines and alkylamido betaines, such as stearamidopropyldimethylamine, diethylaminoethylstearamide, dimethylstearamine, dimethylsoyamine, soyamine, myristylamine, tridecylamine, ethylstearylamine, N-tallowpropane diamine, ethoxylated (5 moles ethylene oxide) stearylamine, dihydroxy ethyl stearylamine, arachidylbehenylamine, and the like. Some suitable betaine surfactants include but are not limited to alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates, and acyl glutamates, wherein the alkyl and acyl groups have from 8 to 18 carbon atoms. Non-limiting examples of preferred amphoteric surfactants include cocamidopropyl betaine, sodium cocoamphoacetate, disodium cocoamphodiacetate, cocamidopropyl hydroxysultaine, and sodium cocoamphopropionate, which are particularly suitable as mild-type cleansers for skin and hair.

Nonionic surfactants are generally uncharged amphiphiles and usually are alkoxylated to varying degrees. Classes of nonionic surfactants include alcohols, alkanolamides, amine oxides, alkyl glucosides, esters, and ethers. Nonionic alcohols are usually hydroxy derivatives of long-chain $C_8$ to $C_{18}$ alkane hydrocarbons, such as cetearyl alcohol, hydrogenated tallow alcohol, lanolin alcohols, alkanolamides, and the like. Alkanolamides contain at least one alkoxyl or one polyoxyethylene grouping and include alkanol-derived amides, such as acylamide DEA, N-alkyl pyrrolidone, palmamide MEA, peanutamide MIPA, and the like and ethoxylated amides, such as PEG-50 tallow amide. Amine oxides include alkylamine oxides, such as lauramine oxide; and acylamidopropyl morpholine oxides, such as cocamidopropylamine oxide; and the like. The alkyl glucosides include linear and branched $C_4$ to $C_{24}$ alkyl glucosides, such as for example nonyl, decyl, dodecyl and lauryl glycoside. Esters include ethoxylated carboxylic acids, such as PEG-8 dilaurate, PEG-8 laurate, and the like; ethoxylated glycerides, such as PEG-4 castor oil, PEG-120 glyceryl stearate, triolein PEG-6 esters, and the like; glycol esters and derivatives thereof, such as glycol stearate SE, propylene glycol ricinoleate, and the like; monoglycerides, such as glyceryl myristate, glyceryl palmitate lactate, and the like; polyglyceryl esters, such as polyglyceryl-6-distearate, polyglyceryl-4 oleyl ether, and the like, polyhydric alcohol esters and ethers, such as methyl glucheth-20 sesquistearate, sucrose distearate; and the like; sorbitan/sorbitol esters, such as polysorbate-20, polysorbate-60, sorbitan sequiisostearate, and the like; and triesters of phosphoric acid, such as trideceth-3 phosphate, trioleth-8 phosphate, and the like. Exemplary ethers include ethoxylated alcohols, such as, Ceteareth-10, Ceteth-10, Ceteth-20, Isoceteth-20, Steareth-10, Steareth-16, Steareth-20, Steareth-25, Oleth-2, Oleth-10, Oleth-20, nonoxynol-9, and the like; ethoxylated lanolin, such as PEG-20 lanolin, PPG-12-PEG-65 lanolin oil, and the like; ethoxylated polysiloxanes, such as dimethicone copolyol, and the like; propoxylated POE ethers, such as meroxapol 314, poloxamer 122, PPG-5-ceteth-20, and the like; and alkyl polyglycosides, such as lauryl glucose, and the like.

Non-limiting examples of nonionic surfactants include linear or branched alcohol ethoxylates, $C_8$ to $C_{12}$ alkylphenol alkoxylates, such as octylphenol ethoxylates, polyoxyethylene polyoxypropylene block copolymers, and the like; $C_8$ to $C_{22}$ fatty acid esters of polyoxyethylene glycol mono- and di-glycerides; sorbitan esters and ethoxylated sorbitan esters; $C_8$ to $C_{22}$ fatty acid glycol esters; block copolymers of ethylene oxide and propylene oxide; and the like. Non-limiting examples of surfactant boosters or hydrotropes include alkanolamides, such as acetamide MEA, monoethanolamide, diethanolamide, lauramide DEA, cocamide MEA, cocamide DEA, isopropanolamide, and the like; amine oxides, such as hydrogenated tallowamine oxide; short chain alkyl aryl sulfonates, such as sodium toluene sulfonate; sulfosuccinates, such as disodium stearyl sulfosuccinate; and the like.

The personal care, home care, health care, and institutional care compositions containing the esters of the present invention in combination with one or more of the foregoing active ingredients and/or with the one or more additives and/or adjuvants, conventionally or popularly included in personal care, health care, home care, and institutional care products discussed above can be prepared as water-free or water-based formulations, and formulations containing water-miscible auxiliary solvents or diluents, but are not limited thereto. Useful solvents commonly employed are typically liquids, such as water (deionized, distilled or purified), alcohols, fatty alcohols, polyols, and the like, and mixtures thereof. Non-aqueous or hydrophobic auxiliary solvents are commonly employed in substantially water-free products, such as nail lacquers, aerosol propellant sprays, or for specific functions, such as removal of oily soils, sebum, make-up, or for dissolving dyes, fragrances, and the like, or are incorporated in the oily phase of an emulsion. Non-limiting examples of auxiliary solvents, other than water, include linear and branched alcohols, such as ethanol, propanol, isopropanol, hexanol, and the like; aromatic alcohols, such as benzyl alcohol, cyclohexanol, and the like; saturated $C_{12}$ to $C_{30}$ fatty alcohol, such as lauryl alcohol, myristyl alcohol, cetyl alcohol, stearyl alcohol, behenyl alcohol, and the like. Non-limiting examples of polyols include polyhydroxy alcohols, such as glycerin, propylene glycol, butylene glycol, hexylene glycol, $C_2$ to $C_4$ alkoxylated alcohols and $C_2$ to $C_4$ alkoxylated polyols, such as ethoxylated, propoxylated, and butoxylated ethers of alcohols, diols, and polyols having about 2 to about 30 carbon atoms and 1 to about 40 alkoxy units, polypropylene glycol, polybutylene glycol, and the like. Non-limiting examples of non-aqueous auxiliary solvents or diluents include silicones, and silicone derivatives, such as cyclomethicone, and the like, ketones such as acetone and methylethyl ketone; natural and synthetic oils and waxes, such as vegetable oils, plant oils, animal oils, essential oils, mineral oils, $C_7$ to $C_{40}$ isoparaffins, alkyl carboxylic esters, such as ethyl acetate, amyl acetate, ethyl lactate, and the like, jojoba oil, shark liver oil, and the like. Some of the foregoing non-aqueous auxiliary solvents or diluents may also be conditioners and emulsifiers.

Where applicable, any known aerosol propellant can be utilized to deliver the personal care, home care, health care and institutional care compositions containing the esters of the present invention in combination with one or more of the foregoing active ingredients and/or with the one or more additives and/or adjuvants, conventionally or popularly included in personal care, health care, home care, and institutional care products discussed above. Exemplary propellants include, but are not limited to lower boiling hydrocarbons such as $C_3$ to $C_6$ straight and branched chain hydrocarbons. Exemplary hydrocarbon propellants include propane, butane, isobutene, and mixtures thereof. Other suitable propellants include ethers, such as, dimethyl ether, hydrofluorocarbons, such as, 1,1-difluoroethane, and compressed gasses, such as air and carbon dioxide. These compositions can contain from about 0.5 to about 60 wt. % of the propellant in one embodiment and from about 0.5 to about 35 wt. % in another embodiment, based on the total weight of the composition.

While overlapping weight ranges for the various components and ingredients that can be contained in the compositions of the invention have been expressed for selected embodiments and aspects of the invention, it should be readily apparent that the specific amount of each component in the disclosed personal care, home care, health care, and institutional care compositions will be selected from its disclosed range such that the amount of each component is adjusted such that the sum of all components in the composition will total 100 wt. %. The amounts employed will vary with the purpose and character of the desired product and can be readily determined by one skilled in the formulation arts and from the literature.

It is also to be recognized that the choice and amount of ingredients in personal care, home care, health care and institutional care compositions that include the esters of the invention can vary depending on the intended product and its function, as is well known to those skilled in the formulation arts. An extensive listing of ingredients and their conventional functions and product categories have been disclosed and can be readily ascertained from the literature, some of which can serve more than one function.

In one embodiment, exemplary cosmetic formulations in which an ester in accordance with the present invention can be added are comprised of at least one carrier (e.g., a volatile carrier) and at least one ester in accordance with the present invention. In another embodiment, another exemplary cosmetic formulation in which an ester in accordance with the present invention can be added is comprised of at least one pigment, at least one carrier (e.g., a volatile carrier) and at least one ester in accordance with the present invention. In still another embodiment, suitable cosmetic and/or personal care formulations for use in combination with the esters of the present invention can include various other known cosmetic and/or personal care additives. Such additives can include, but are not limited to, one or more emollients, one or more solvents, one or more structuring agents (e.g., a wax), and one or more preservatives.

One such exemplary cosmetic formulation for a lipstick is shown below. Again, it should be noted that the present invention is not limited to just the formulation shown below. Rather, the present invention should be broadly construed.

| Components: Part A | | |
|---|---|---|
| Component Trade Name | Weight Percent | Function |
| Red 7 Lake, Softex D&C Red No. 7 Calcium Lake | 5.42 | Pigment |
| *Ricinos Communis* (Castor) Seed Oil, Castor Oil Pale Pressed | 10.08 | Emollient/Solvent |

| Components: Part B | | |
|---|---|---|
| Component Trade Name | Weight Percent | Function |
| One of the following Schercemol ™ PDD, DIS, TISC, or PTID Esters or Experimental Esters 1, 2, 3, 4, or 5 | 58.7 | Emollient/Solvent |
| *Copernica Cerifera* (Carnauba) Wax, Carnauba Wax | 1.50 | Structuring Agent |
| *Euphorbia Cerifera* (Candelilla) Wax, Candelilla Wax | 6.00 | Structuring Agent |
| Ozokerite, Ozokerite Wax Pastilles | 2.50 | Structuring Agent |
| Microcrystalline Wax, Microcrystalline Wax | 3.50 | Structuring Agent |
| Methylparaben | 0.20 | Preservative |
| Propylparaben | 0.10 | Preservative |

| Component: Part C | | |
|---|---|---|
| Component Trade Name | Weight Percent | Function |
| Mica, Titanium Dioxide, Pearlescent Pigment Prestige Red | 12.00 | Pearlescent Pigment |

Parts A, B, and C add up to 100 weight percent. Regarding the above-identified Schercemol Esters, such compounds are available from The Lubrizol Corporation of Wickliffe, Ohio. In particular, the Schercemol™ Esters discussed above are as follows: Schercemol™ PDD Ester (INCI Name: diisostearoyl polyglyceryl-3 dimer dilinoleate); Schercemol™ DIS Ester (INCI Name: diisopropyl sebacate); Schercemol™ TISC Ester (INCI Name: triisostearyl citrate); and Schercemol™ PTID Ester (INCI Name: triisostearoyl polyglyceryl-3 dimer dilinoleate). Regarding the above-identified Experimental Esters they are as follows: Experimental Ester 1 (tris(glyceryl diisostearate) trimellitate); Experimental Ester 2 (tris(glyceryl diisostearate) citrate); Experimental Ester 3 (tris(TMP diisostearate) trimellitate); Experimental Ester 4 (tris(polyglyceryl-3-tetraisostearate) citrate); and Experimental Ester 5 (Bis(Trimethylolpropyl Dicocoate) Adipate).

The procedure for producing a lipstick in accordance with the above formulation is as follows. Combine Part A ingredients with mixing and heat to about 60° C. to about 65° C. In a separate mixing vessel, combine Part B ingredients with mixing and heat to about 60° C. to about 65° C. Allow to mix until homogenous. Once the above temperatures are achieved and mixtures homogenous, add Part B to Part A with continued mixing. Allow to cool to below 40° C. Add Part C to Parts A and B with mixing.

Lipstick Wear Test:
Wear Bolt Test:
(1) Place 15 grams of the lipstick in a 57 mm aluminum pan;
(2) Melt the lipstick in the pan;
(3) Cool the lipstick to room temperature and make sure the surface is flat;
(4) Heat the lipstick to about 35° C. to 37° C. and check the surface temperature with an Infrared non-contact thermometer;
(5) Place a one and one-half inch pre-weighted (to five places after the decimal) circular paper towel on the warmed lipstick surface;
(6) Place a 500 gm standard weight on the paper towel and rotate the weight 360 degrees;

(7) Pick off the paper towel and weigh it to five places after the decimal; and (8) Determine the increase in weight of the paper towel after lipstick transfer.

The results of the above test indicate that the esters of the present invention have much better wear properties than those made with various commercially available esters. For example, lipstick made with DIS (MW equal to 286) has a much higher transfer to a paper towel than the Experimental Esters 1 through 4 with a minimum molecular weight of at least 1,500 daltons. The commercial Schercemol™ PDD, PTID and TISC esters also show less transfer to the paper towel, however they do not fare as well in tack tests when compared to the ester compositions of the present invention.

Determining Tack of the Neat Esters:

The tack for the neat Schercemol™ PDD, PTID, TISC and DIS esters and the Experimental Esters 1 through 5 are determined as follows.

A four mill draw down is made with the above mentioned esters on a glass plate. The Rolling Ball tack determination based on the ASTM Method D 3121-06 is used to determine the tack for each ester. The longer the ball travel the less tacky the ester. If the ester is too low in viscosity to form a homogeneous four mill drawdown this low viscosity ester is added to a Schercemol™ PDD ester at various concentrations. The ball travel versus concentration is plotted and extrapolation to zero concentration of Schercemol™ PDD ester is made to determine the tack of the neat low viscosity ester. The results thereof are shown in Table 2 below.

TABLE 2

| Neat Ester Tested | Ball Travel (cm) |
| --- | --- |
| Schercemol ™ PDD Ester | 2.8 |
| Schercemol ™ PTID Ester | 8.8 |
| Schercemol ™ TISC Ester | 9.4 |
| Schercemol ™ DIS Ester | 39.0 |
| Experimental Ester 1 | 15.4 |
| Experimental Ester 2 | 23.7 |
| Experimental Ester 3 | 16.5 |
| Experimental Ester 4 | 16.4 |
| Experimental Ester 5 | 17.7 |

The invention is to have an ester with longer wear than low molecular weight esters like DIS but that is also less tacky than the commercial esters like PDD, PTID and TISC. The five experimental esters with branched chemical architecture exhibit longer wear than DIS but also less tack than other higher molecular weight esters like PDD, PTID, and TISC.

Additional testing procedures for various cosmetic and/or personal care formulations are disclosed in U.S. Pat. No. 6,406,683, which is hereby incorporated by reference in its entirety. Tests disclosed in U.S. Pat. No. 6,406,683 which can be used in conjunction with cosmetic and/or personal care formulations containing one or more esters in accordance with those of the present invention include: (1) a Dry Blot and Rub Test that predicts the ability of a cosmetic film to resist color transfer upon contact with certain objects; (2) Oil Blot and Rub Test Method which predicts the ability of a cosmetic film to resist color transfer to oily fingers or objects such as oily foods; and (3) Flexibility Test Method which is measured by the latex stretch test and predicts the ability of the color film to resist flaking or peeling types of failure after application by movement during normal activities.

While in accordance with the patent statutes the best mode and certain embodiments of the invention have been set forth, the scope of the invention is not limited thereto, but rather by the scope of the attached. As such, other variants within the spirit and scope of this invention are possible and will present themselves to those skilled in the art.

What is claimed is:

1. An ester compound for use in a personal care, home care, health care, and institutional care composition which is the reaction product of:

at least one poly-alcohol selected from the group consisting of glycerol, polyglycerol containing from 2 to 20 glycerol units, pentaerythritol, dipentaerythrityl, tripentaerythritol, trimethylolpropane, neopentyl glycol, propylene glycol, 1,3-butylene glycol, 2-methyl-1,3-propanediol, dipropylene glycol, ethylene glycol, cyclohexane-dimethanol, butyl ethyl propanediol, resorcinol, hydroquinone, dimethylolpropanoic acid, dimethylol butanoic acid, and combinations thereof;

at least one mono-carboxylic acid; and at least one poly-carboxylic acid selected from the group consisting of oxalic acid, malonic acid, succinic acid, glutaric acid, azelaic acid, dodecanedioic acid, maleic acid, fumaric acid, phthalic acid, isophthalic acid, terephthalic acid, 2,6-naphthalene dicarboxylic acid, citric acid, malic acid, tartaric, butane tertracarboxylic acid, phthalic anhydride, trimellitic anhydride, succinic anhydride, maleic anhydride, derivatives thereof or combinations thereof, wherein the resulting ester has a molecular weight of 1,500 to 100,000 daltons and a viscosity of less than 1000 mPa·s measured at 20 to 25° C.

2. The ester compound of claim 1, wherein the at least one mono-carboxylic acid is selected from one or more compounds according to the formula $R_5C(O)OH$, where $R_5$ is selected from a linear or branched, substituted or unsubstituted $C_1$ to $C_{60}$ hydrocarbyl group.

3. The ester compound of claim 2, wherein $R_5$ is selected from linear or branched, substituted or unsubstituted $C_1$ to $C_{60}$ alkyl groups, substituted or unsubstituted $C_3$ to $C_{10}$ cycloalkyl groups, linear or branched, substituted or unsubstituted $C_2$ to $C_{60}$ alkenyl groups, substituted or unsubstituted $C_3$ to $C_{10}$ cycloalkenyl, linear or branched, substituted or unsubstituted $C_2$ to $C_{60}$ alkynyl groups, substituted or unsubstituted $C_6$ to $C_{17}$ aryl groups, and linear or branched $C_2$ to $C_{60}$ ester residues.

4. A personal care composition comprising an ester compound of claim 1 in combination with an active ingredient selected from vitamins, anti-stretch mark compounds, astringents, draining compounds, hair growth compounds, skin and hair nourishing compounds, skin and hair protecting compounds, self-tanning compounds, skin lighteners, lip plumping compounds, anti-aging compounds, anti-cellulite compounds, anti-acne compounds, anti-dandruff compounds, anti-inflammatory compounds, analgesics, antioxidant compounds, antiperspirant compounds, deodorant compounds, hair fixative polymers, hair and skin conditioners; and combinations thereof.

5. A personal care composition of claim 4, wherein said composition is a product selected from lipstick, foundation makeup, eye shadow, blush, eyeliner, mascara, and concealer.

6. The ester compound of claim 1, wherein said viscosity ranges from 100 mPa·s to less than 1000 mPa·s measured at 20 to 25° C.

7. The ester compound of claim 1, which is the reaction product of glycerol, trimellitic anhydride and isostearic acid.

8. The ester compound of claim 1, which is the reaction product of glycerol, citric acid and isostearic acid.

9. The ester compound of claim 1, which is the reaction product of trimethylolpropane, trimellitic anhydride and isostearic acid.

10. The ester compound of claim 1, which is the reaction product of polyglycerol-3, citric acid and isostearic acid.

11. An ester compound for use in a personal care, home care, health care, and institutional care composition comprising the reaction product of:
- a poly-alcohol selected from the group consisting of glycerol, polyglycerol containing from 2 to 20 glycerol units, pentaerythritol, dipentaerythrityl, tripentaerythritol, trimethylolpropane, neopentyl glycol, propylene glycol, 1,3-butylene glycol, 2-methyl-1,3-propanediol, dipropylene glycol, ethylene glycol, cyclohexane-dimethanol, butyl ethyl propanediol, resorcinol, hydroquinone, dimethylolpropanoic acid, dimethylol butanoic acid, and combinations thereof;
- a mono-carboxylic acid selected from coconut fatty acid; and
- a poly-carboxylic acid selected from the group consisting of oxalic acid, malonic acid, succinic acid, glutaric acid, adipic acid, azelaic acid, sebacic acid, dodecanedioic acid, maleic acid, fumaric acid, phthalic acid, isophthalic acid, terephthalic acid, 2,6-naphthalene dicarboxylic acid, citric acid, malic acid, tartaric, butane tertracarboxylic acid, phthalic anhydride, trimellitic anhydride, succinic anhydride, maleic anhydride, derivatives thereof or combinations thereof, wherein the resulting ester has a molecular weight of 1,500 to 100,000 daltons and a viscosity of 100 mPa·s to less than 1000 mPa·s measured at 20 to 25° C.

12. The ester compound of claim 11, which is the reaction product of trimethylolpropane, adipic acid and coconut fatty acid.

* * * * *